US012678592B2

(12) United States Patent (10) Patent No.: US 12,678,592 B2
Lerner (45) Date of Patent: Jul. 14, 2026

(54) DUAL LUMEN CATHETER

(71) Applicant: Nuwellis, Inc., Eden Prairie, MN (US)

(72) Inventor: David Lerner, St. Paul, MN (US)

(73) Assignee: Nuwellis, Inc., Eden Prairie, MN (US)

( * ) Notice: Subject to any disclaimer, the term of this patent is extended or adjusted under 35 U.S.C. 154(b) by 218 days.

(21) Appl. No.: 18/259,973

(22) PCT Filed: Dec. 30, 2021

(86) PCT No.: PCT/US2021/073199
§ 371 (c)(1),
(2) Date: Jun. 29, 2023

(87) PCT Pub. No.: WO2022/147476
PCT Pub. Date: Jul. 7, 2022

(65) Prior Publication Data
US 2024/0075247 A1 Mar. 7, 2024

Related U.S. Application Data

(60) Provisional application No. 63/199,486, filed on Dec. 31, 2020.

(51) Int. Cl.
*A61M 25/00* (2006.01)

(52) U.S. Cl.
CPC ...... *A61M 25/005* (2013.01); *A61M 25/0052* (2013.01); *A61M 2025/0035* (2013.01); *A61M 2025/0037* (2013.01)

(58) Field of Classification Search
CPC .. A61M 2025/0035; A61M 2025/0037; A61M 25/0052
See application file for complete search history.

(56) References Cited

U.S. PATENT DOCUMENTS 4,610,656 A * 9/1986 Mortensen ........... A61M 60/113
604/6.14
4,623,327 A * 11/1986 Mahurkar ........... A61M 5/1582
604/44

(Continued)

FOREIGN PATENT DOCUMENTS

DE 4105965 C2 * 6/1993 .......... A61M 5/1582
DE 102008052752 A1 * 4/2010 ........ A61M 25/0023

(Continued)

OTHER PUBLICATIONS

"International Application Serial No. PCT/US2021/073199, International Search Report mailed May 17, 2022", 5 pgs.

(Continued)

*Primary Examiner* — Bhisma Mehta
*Assistant Examiner* — Adam J. Cermak
(74) *Attorney, Agent, or Firm* — Schwegman Lundberg & Woessner, P.A.

(57) ABSTRACT

A catheter may include a withdrawal lumen wall extending around a withdrawal lumen. The withdrawal lumen may have a withdrawal lumen profile. The catheter may include an infusion lumen wall coupled with the withdrawal lumen wall. The infusion lumen wall may extend around an infusion lumen. The infusion lumen may have an infusion lumen profile smaller than the withdrawal lumen profile. A flexible septum may extend between the withdrawal lumen and the infusion lumen. The flexible septum may isolate the withdrawal lumen from the infusion lumen. In another example, a blood filtration system may monitor blood flow velocity within vasculature. The blood filtration system may guide operation of a blood pump or a filtrate bump based on the blood flow velocity within the vasculature.

11 Claims, 16 Drawing Sheets

(56)                    References Cited

U.S. PATENT DOCUMENTS

|  |  |  |  |  |  |
|---|---|---|---|---|---|
| 4,895,561 | A * | 1/1990 | Mahurkar | ........... | A61M 1/3653 604/533 |
| 5,989,206 | A * | 11/1999 | Prosl | .................. | A61M 1/3653 604/523 |
| 6,126,631 | A * | 10/2000 | Loggie | ............. | A61M 25/0026 604/264 |
| 7,135,008 | B2 | 11/2006 | O'Mahony et al. | | |
| 10,238,836 | B2 * | 3/2019 | Sansoucy | ............. | B29C 48/001 |
| 2004/0084050 | A1 * | 5/2004 | Baran | ................. | A61M 11/001 128/207.14 |
| 2004/0097863 | A1 * | 5/2004 | Appling | ........... | A61M 25/0026 604/524 |
| 2004/0254528 | A1 * | 12/2004 | Adams | .............. | A61M 25/0029 604/96.01 |
| 2005/0119597 | A1 * | 6/2005 | O'Mahony | ......... | A61M 1/3661 604/4.01 |
| 2005/0148929 | A1 * | 7/2005 | Gingles | ................ | A61M 31/00 604/95.04 |
| 2006/0020256 | A1 * | 1/2006 | Bell | .................. | A61M 25/0052 604/523 |
| 2006/0270962 | A1 * | 11/2006 | McGuckin, Jr. | ............................ A61M 25/09041 604/533 |
| 2007/0088319 | A1 * | 4/2007 | Martone | ........... | A61M 25/0662 606/108 |
| 2007/0106206 | A1 * | 5/2007 | Appling | ............ | A61M 25/0068 604/6.16 |
| 2008/0097350 | A1 * | 4/2008 | Bell | .................. | A61M 25/0032 604/266 |
| 2008/0103480 | A1 * | 5/2008 | Bosel | .................. | A61M 25/003 604/513 |
| 2008/0195021 | A1 * | 8/2008 | Roger | ................. | A61M 1/3639 604/4.01 |
| 2009/0043240 | A1 * | 2/2009 | Robinson | ............... | A61B 5/155 604/6.11 |
| 2009/0118661 | A1 * | 5/2009 | Moehle | ............. | A61M 25/0032 604/6.16 |
| 2009/0204079 | A1 * | 8/2009 | Nimkar | ............... | A61M 25/001 604/246 |
| 2009/0247868 | A1 * | 10/2009 | Chesnin | ............ | A61M 25/0032 604/523 |
| 2011/0004198 | A1 * | 1/2011 | Hoch | ................ | A61M 25/0026 604/523 |
| 2011/0137225 | A1 * | 6/2011 | Feng | .................. | A61M 1/3659 604/6.16 |
| 2011/0160721 | A1 * | 6/2011 | Wang | ................. | A61B 18/1492 606/41 |
| 2012/0041419 | A1 * | 2/2012 | Blanchard | ........... | A61M 25/003 604/523 |
| 2013/0261605 | A1 * | 10/2013 | Gregersen | ......... | A61M 25/0009 156/303.1 |
| 2013/0304033 | A1 * | 11/2013 | DeFonzo | ............ | A61M 1/3653 604/524 |
| 2015/0360000 | A1 * | 12/2015 | Sansoucy | .......... | A61M 25/0102 264/154 |
| 2016/0250451 | A1 * | 9/2016 | Purdy | ........................ | A61F 7/12 604/506 |
| 2019/0321110 | A1 * | 10/2019 | Grunwald | .............. | A61B 8/488 |
| 2020/0022587 | A1 * | 1/2020 | Glover | ................. | A61B 5/6869 |
| 2025/0128024 | A1 * | 4/2025 | Sansoucy | ............... | B29C 48/91 |

FOREIGN PATENT DOCUMENTS

| | | | | |
|---|---|---|---|---|
| EP | | 1433493 A2 * | 6/2004 | .......... A61M 11/001 |
| WO | WO-2020198483 A1 | | 10/2020 | |
| WO | WO-2022147476 A1 | | 7/2022 | |

OTHER PUBLICATIONS

"International Application Serial No. PCT/US2021/073199, Invitation to Pay Additional Fees mailed Mar. 14, 2022", 2 pgs.

"International Application Serial No. PCT/US2021/073199, Written Opinion mailed May 17, 2022", 14 pgs.

International Application Serial No. PCT/US2021/073199, International Preliminary Report on Patentability mailed Mar. 6, 2024, 21 pgs.

* cited by examiner

DUAL LUMEN CATHETER

CLAIM FOR PRIORITY

This application is a U.S. national stage filing under 35 U.S.C. § 371 from International Application No. PCT/US2021/073199, filed on Dec. 30, 2021, and published as WO 2022/147476 on Jul. 7, 2022, which claims the benefit of priority of U.S. Application Ser. No. 63/199,486, filed Dec. 31, 2020, the benefit of priority of each of which is claimed herein, and which applications and publication are hereby incorporated herein by reference in their entirety.

TECHNICAL FIELD

This document pertains generally, but not by way of limitation, to a catheter, for instance a dual lumen catheter for a blood filtration system.

BACKGROUND

A catheter may include a withdrawal lumen and an infusion lumen. A catheter may be used to withdraw blood from a patient, for example with the withdrawal lumen. The catheter may be used to infuse blood into the patient, for example with the infusion lumen.

SUMMARY

The present inventors have recognized, among other things, that a problem to be solved can include reducing recirculation between an infusion lumen of a catheter and a withdrawal lumen of a catheter. Additionally, the present inventors have recognized, among other things, that a problem to be solved can include reducing withdrawal resistance in a blood circuit. The present subject matter can help provide a solution to these problems, such as by providing a catheter with an infusion lumen tip longitudinally offset from a withdrawal lumen tip. In an example, the catheter may include an infusion lumen wall extending to the infusion lumen tip. The infusion lumen wall may surround an infusion lumen. The infusion lumen may be configured for fluidic communication with an infusion line of a blood filtration system. The infusion lumen may be configured to discharge fluid at the infusion lumen tip. The fluid may be supplied by the blood filtration system.

The catheter may include a withdrawal lumen wall extending to the withdrawal lumen tip. The withdrawal lumen wall may surround a withdrawal lumen. The withdrawal lumen may be configured for fluidic communication with a withdrawal line of the blood filtration system. The infusion lumen may be isolated from the withdrawal lumen. The withdrawal lumen may be configured to receive fluid from vasculature of a patient at the withdrawal lumen tip. The withdrawal lumen wall extends beyond the infusion lumen tip, for example to longitudinally offset the withdrawal lumen tip from the infusion lumen tip.

Longitudinally offsetting the withdrawal lumen tip from the infusion lumen tip reduces recirculation from the infusion lumen to the withdrawal lumen. For example, the blood filtration system may hemoconcentrate blood, for instance due to filtration of one or more plasma constituents from the blood. The hemoconcentrated blood may be provided to the infusion lumen of the catheter to infuse the hemoconcentrated blood into the vasculature. In some approaches, the hemoconcentrated blood is drawn into the withdrawal lumen, and the hemoconcentrated blood enters a blood circuit of the blood filtration system (where it may be further hemoconcentrated). Hemoconcentration of the blood may lead to clotting within the blood circuit (e.g., clotting of a filter configured to remove one or more plasma constituents from the blood). Accordingly, longitudinally offsetting the withdrawal lumen tip from the infusion lumen tip reduces recirculation of hemoconcentrated blood from the infusion lumen to the withdrawal lumen. Thus, clotting in the blood circuit may be minimized, and a lifetime (e.g., operating duration, or the like) of the blood circuit may be enhanced.

The blood filtration system may include a blood circuit. For instance, the blood circuit may include (but is not limited to) the catheter, an infusion line, a filter, and a withdrawal line. Resistance in the blood circuit (e.g., resistance in a withdrawal lumen of the catheter) may correspond to a resistance of flow of a liquid, such as blood, within the blood circuit. For example, a withdrawal lumen resistance characteristic may correspond to an amount of resistance in the withdrawal lumen to the flow of blood through withdrawal lumen. In some approaches, extending a length dimension of the withdrawal lumen increases the withdrawal lumen resistance characteristic. In an example, an increase in a cross-sectional area of the withdrawal lumen reduces the withdrawal lumen characteristic. Accordingly, a change (e.g., increase, or the like) in the withdrawal resistance characteristic may be minimized by increasing the cross-sectional area of the withdrawal lumen to offset the increase in the withdrawal lumen resistance characteristic due to the change in the length dimension of the withdrawal lumen. In an example, the minimization of withdrawal resistance allows the catheter to reach arteries of the patient. An artery may have a greater amount of blood flow in comparison to the amount of blood flow in a vein. The blood filtration system may withdraw blood from the artery using the catheter. For instance, withdrawing blood from an artery may reduce stagnation of blood within the blood circuit. Thus, performance of the blood filtration system may be enhanced with the catheter, for instance because the catheter reduces clotting of blood in the blood circuit.

In another example, the present inventors have recognized, among other things, that a problem to be solved can include enhancing flow within a catheter. Enhancing flow within the catheter may reduce stagnation of blood within the blood circuit. For instance, a catheter may include a flexible septum between a withdrawal lumen and an infusion lumen. In some approaches, the flexible septum may deflect toward the withdrawal lumen. For instance, deflection of the flexible septum toward the withdrawal lumen may reduce blood flow between the catheter and other components of the blood filtration system. For instance, the blood may stagnate within the blood circuit. The reduction in blood flow through the components may cause the blood to clot within the components of the blood filtration system (e.g., the blood circuit, the filter, or the like). In this approach, blood may clot within the components of the blood filtration system due to blood stasis within the components. Thus, the components may be replaced to resume operation of the blood filtration system.

The present subject matter can help provide a solution to this problem, for example with a catheter having a flexible septum. The catheter may inhibit deflection of the flexible septum toward the withdrawal lumen of the catheter. Accordingly, resistance to flow within the withdrawal lumen may be minimized. Thus, blood flow in the withdrawal lumen (and other components of the blood circuit) may be enhanced. Enhancing blood flow in the withdrawal lumen may reduce blood stasis within the withdrawal lumen (and other components of the blood circuit).

In an example, the catheter may include a withdrawal lumen wall extending around a withdrawal lumen. The withdrawal lumen may have a withdrawal lumen profile. The catheter may include an infusion lumen wall. For instance, the infusion lumen wall may be coupled with the withdrawal lumen wall. The infusion lumen wall may extend around an infusion lumen. In another example, the infusion lumen may have an infusion lumen profile smaller than the withdrawal lumen profile.

The catheter may include a flexible septum. For instance, the flexible septum may extend between the withdrawal lumen and the infusion lumen. The flexible septum may be coupled with the withdrawal lumen wall and the infusion lumen wall. The flexible septum may isolate the withdrawal lumen from the infusion lumen. The difference between the infusion lumen profile and the withdrawal lumen profile may inhibit deflection of the septum toward the withdrawal lumen. For instance, the difference between the infusion lumen profile and the withdrawal lumen profile may augment the transmural pressure (against the septum) within the withdrawal lumen. For instance, the transmural pressure in the withdrawal lumen may be greater than the transmural pressure within the infusion lumen. The difference in transmural pressure may inhibit deflection of the septum toward the withdrawal lumen. The difference in transmural pressure may deflect the septum toward the infusion lumen. Thus, the resistance to blood flow within the withdrawal lumen may be minimized, and performance of the blood filtration system is enhanced by reducing stagnation (or stasis) of blood within components of the blood circuit.

In yet another example, the present inventors have recognized, among other things, that a problem to be solved can include reducing stagnation within a blood circuit. For instance, blood may stagnate within the blood circuit in correspondence with the blood flow rate (through the blood circuit) exceeds the flow rate through the vein of the patient. In an example, pressure in the withdrawal lumen may increase as the blood flow rate approaches the flow rate through the vein of the patient. In an approach, the pressure in the withdrawal lumen may exceed a pressure threshold, and the blood filtration system may stop the blood pump (and correspondingly stop flow within the blood circuit). Accordingly, blood may stagnate in the blood circuit. Stagnation of blood may lead to loss of the blood circuit. For instance, blood may clot in the filter. The filter may be replaced to resume operation of the blood filtration system.

The present subject matter can help provide a solution to this problem, for example by guiding one or more of blood flow rate or the extraction rate in correspondence with flow through the vein of the patient. In an example, a blood filtration system may include a blood circuit. The blood circuit may include a catheter. The catheter may be inserted into vasculature of a patient. The catheter may include a transducer. The transducer may measure one or more fluid flow characteristics of fluid flowing in the vasculature of the patient, for instance with the catheter inserted into the vasculature of the patient.

The blood filtration system may include a controller. The controller may include a sensor interface module. The sensor interface module may receive the measured fluid flow characteristics from the transducer. The controller may include a pump module. The pump module may modulate one or more of a variable-speed blood pump or a variable-speed filtration pump. In an example, the pump module may modulate the variable-speed blood pump to vary a blood flow rate through the blood circuit. In another example, the pump module may modulate the variable-speed filtrate pump to vary an extraction rate of filtrate fluid from a filter of the blood circuit.

The controller may include a therapy guidance module. The therapy guidance module may guide one or more of the blood flow rate or the extraction rate. For instance, the therapy guidance module may change the blood flow rate based on the one or more fluid flow characteristics. In another example, the therapy guidance module is configured to change the extraction rate based on the one or more fluid flow characteristics. Accordingly, the blood filtration system may reduce stagnation in the blood circuit, for instance by changing one or more of the blood flow rate or the extraction rate based on the monitored fluid flow characteristics of fluid in vasculature of the patient.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
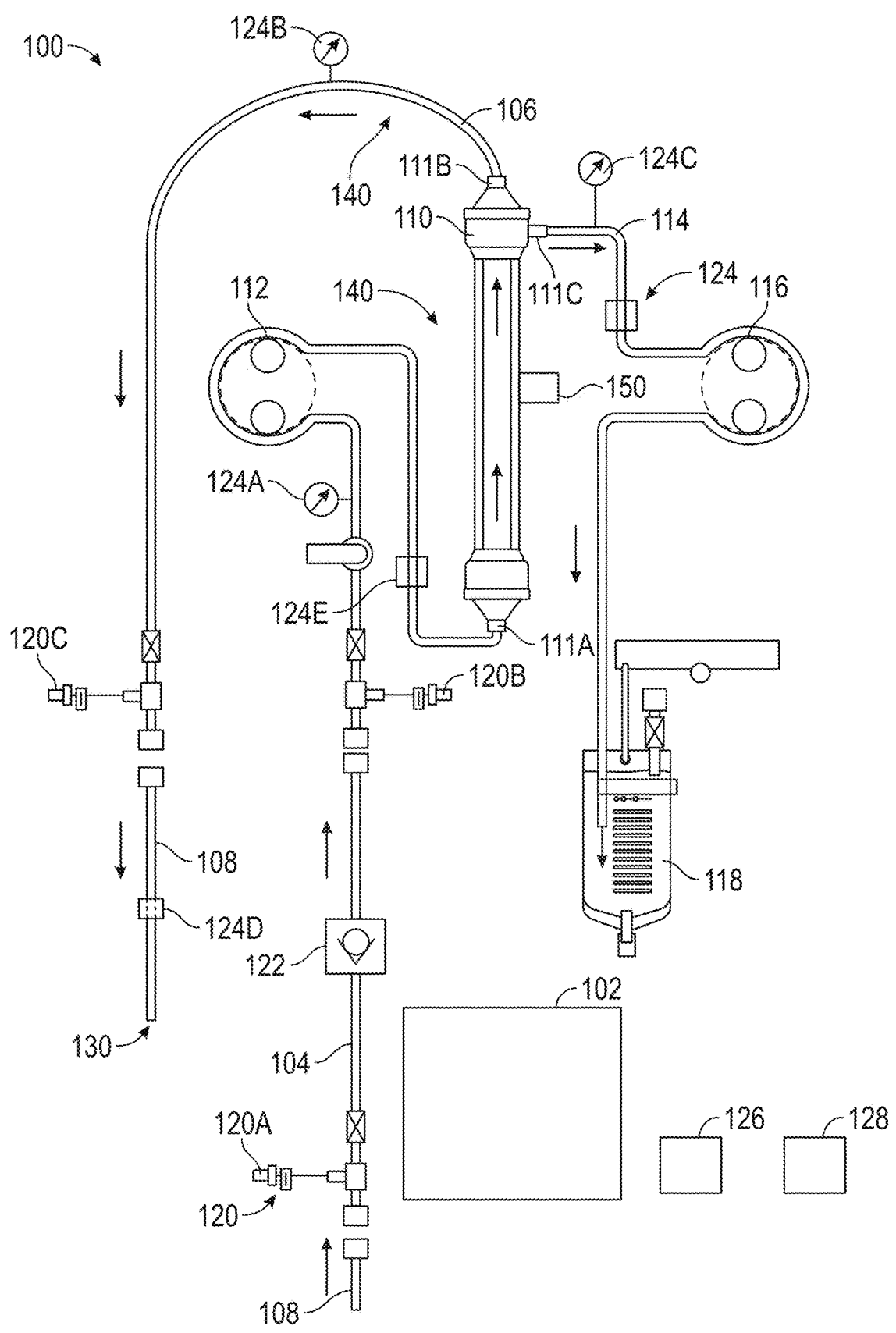
FIG. 1 shows a schematic view of an example of a blood filtration system, according to an embodiment of the present subject matter.

FIG. 1 shows a schematic view of an example of portions of a blood filtration system 100, according to an embodiment of the present subject matter. The blood filtration system 100 may reduce one or more plasma constituents (e.g., water, proteins, electrolytes, or the like) in blood of a patient. The blood filtration system 100 may facilitate one or more blood filtration operations, including (but not limited to): extracorporeal ultrafiltration, continuing renal replacement therapy ("CRRT"), slow continuous ultrafiltration ("SCUF"), continuous veno-venous hemofiltration ("CVVH"), continuous veno-venous hemofiltration ("CVVHD"), dialysis, continuous veno-venous hemofiltration including dialysis and filtration ("CVVHDF"), sustained low efficiency dialysis ("SLED"), extracorporeal membrane oxygenation ("ECMO") therapy, modified ultrafiltration, and peripheral plasmapheresis, peripheral hemofiltration.

The blood filtration system 100 may include a controller 102. The controller 102 may include processing circuitry, for instance an integrated circuit. As described herein, the controller 102 may operate one or more components of the blood filtrations system 100.

The blood filtration system 100 may include a withdrawal line 104 and may include an infusion line 106. The lines 104, 106 may be configured to couple with a catheter 108, and the lines 104, 106 may transmit blood within the blood filtration system 100. In an example, the catheter 108 may be inserted into a blood stream of the patient, for instance the catheter 108 may be inserted into a basilic vein, cephalic vein, brachial vein, the axillary vein, the subclavian vein, the brachiocephalic vein, or the like. Blood may flow into the catheter 108, into the withdrawal line 104, through other components of the system 100, through the infusion line 106, into the catheter 108, and back into the blood stream of the patient. The line 104 may be separate from the line 106. The lines 104, 106 may be in fluidic communication with the catheter 108. For example, the catheter 108 may include one or more lumens, for example a withdrawal lumen in fluidic communication with the line 104 and an infusion lumen in fluidic communication with the line 106.

The lines 104, 106 may be configured to couple with a filter 110, for instance the lines 104, 106 may include one or more fittings that facilitate coupling the lines 104, 106 with the filter 110. In an example, the withdrawal line 104 may couple with a filter inlet port 111A, and the infusion line 106 may couple with a filter outlet port 111B. The filter 110 may be configured to reduce an amount of one or more plasma constituents (e.g., water, electrolytes, or the like) in blood flowing through the filter 110 and provide a filtrate fluid including the one or more plasma constituents. As described herein, blood may flow through the lines 104, 106 to and from the catheter 108. The lines 104, 106 may be coupled with the filter and blood may flow from the withdrawal line 104, through the filter 110, and into the infusion line 106.

The blood filtration system 100 may include a blood pump 112, and the blood pump 112 may drive (e.g., convey, pump, push, pull, or the like) blood through the blood filtration system 100. In an example, the blood pump 112 may be a peristaltic pump, and the blood pump 112 may engage with the withdrawal line 104 to drive blood through the withdrawal line 104 and into the filter 110. The controller 102 may be configured to operate the blood pump 112 to vary a speed of the blood pump 112 and accordingly vary the flow rate of blood through the blood filtration system 100 (e.g., the withdrawal line 104, the filter 110, the infusion line 106, or the like).

Referring again to FIG. 1, the blood filtration system 100 may include a filtration line 114 and a filtration pump 116. The filtration line 114 may be configured to couple with the filter 110 (e.g., with a fitting), for instance the filtration line 114 may couple with a filtrate fluid port 111C. The filter 110 may be configured to transmit the filtrate fluid (including one or more plasma constituents) extracted by the filter 110 to the filtrate fluid port 111C.

The filtration pump 116 may drive extracted filtrate fluid from the filter 110, and into a filtrate fluid reservoir 118 (e.g., a bag, container, bladder, or the like). In some examples, the filtration pump 116 may be a peristaltic pump that engages with the filtration line 114 to pump the filtrate fluid through the filtrate fluid line 114. The controller 102 may be configured to vary a speed of the filtration pump 116 and accordingly vary the flow rate of filtrate fluid through the blood filtration system 100 (e.g., the filtration line 114).

The system 100 may include a blood circuit 120, and the blood circuit 120 may include one or more components of the system 100, such as may provide a conduit for blood flow. For example, the blood circuit 120 may include (but is not limited to) the withdrawal line 104, the infusion line 106, the catheter 108, the filter 110, the filtration line 114, the filtrate fluid reservoir 118. The blood circuit 120 may include components of the system 100 that are in communication with a biological fluid of the patient.

Figure 2:
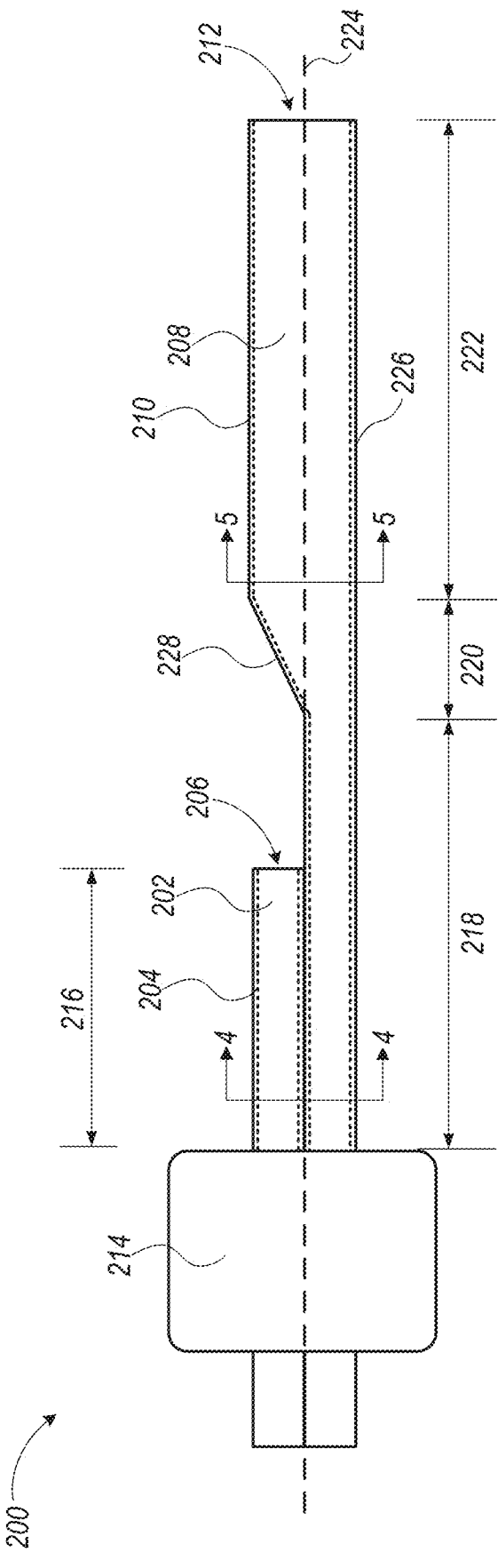
FIG. 2 shows a side view of an example of a dual lumen catheter, according to an embodiment of the present subject matter.

FIG. 2 shows a side view of an example of a dual lumen catheter 200, according to an embodiment of the present subject matter. In some examples, the blood filtration system 100 includes the dual lumen catheter 200. For instance, the blood circuit 120 may include the dual lumen catheter 200. The dual lumen catheter 200 may couple with one or more of the withdrawal line 104 or the infusion line 106.

In an example, the dual lumen catheter 200 includes an infusion lumen 202. The infusion lumen 202 may be in fluidic communication with the infusion line 106. For example, the infusion lumen 202 may facilitate infusion of fluid into vasculature, for instance blood supplied by the blood filtration system 100. An infusion lumen wall 204 may surround the infusion lumen 202. The infusion lumen wall 204 may extend to an infusion lumen tip 206. The infusion lumen 202 may infuse fluid, for example filtered blood, into vasculature of a patient. For instance, the blood pump 112 may generate a positive pressure in the infusion line 106 to infuse (e.g., provide, pump, supply, force, push, pull, blow, or the like) fluid through the infusion line 106, into the infusion lumen 202 of the catheter 200 and out of the infusion lumen 202 proximate the infusion lumen tip 206. Accordingly, the infusion lumen 202 of the catheter 200 supplies fluid from the blood filtration system 100, for example by infusing filtered blood into a patient.

The dual lumen catheter 200 includes a withdrawal lumen 208. The withdrawal lumen 208 may facilitate withdrawal of fluid, such as blood, from vasculature of a patient. For example, a withdrawal lumen wall 210 may surround (e.g., enclose, encircle, encompass, define, or the like) the withdrawal lumen 208. The withdrawal lumen wall 210 may extend to a withdrawal lumen tip 212. The blood pump 112 (shown in FIG. 1) may generate a negative pressure within the withdrawal line 104. The withdrawal lumen 208 may be in fluidic communication with the withdrawal line 104. Accordingly, the blood pump 112 may generate a negative pressure within the withdrawal lumen 208 of the dual lumen catheter 200. The negative pressure within the withdrawal lumen 208 may draw (e.g., entrain, provide, pump, suck, push, pull, or the like) fluid, such as blood, into the withdrawal lumen 208. Thus, the withdrawal lumen 208 of the catheter 200 facilitates withdrawing fluid from vasculature of a patient, and supplying the fluid to the blood filtration system 100.

The dual lumen catheter 200 may include a hub 214. The hub 214 may enhance the structural strength of the catheter 200, for instance to facilitate the insertion of the catheter 200 (e.g., the infusion lumen tip 206 and the withdrawal lumen tip 212, or the like) into vasculature of a patient. The infusion lumen wall 204 and the withdrawal lumen wall 210 may be coupled with the hub 214. The infusion lumen 202 and the withdrawal lumen 208 may extend through the hub 214.

As described herein, the dual lumen catheter 200 includes the infusion lumen wall 204 and the withdrawal lumen wall 210. The infusion lumen tip 206 may be longitudinally offset from withdrawal lumen tip 212. For instance, the infusion lumen wall 204 may include a proximal section 216. In an example, the proximal section 216 of the infusion lumen wall 204 may extend from the hub 214 to the infusion lumen tip 206. The withdrawal lumen wall 210 may include a proximal section 218. In an example, the proximal section 218 of the withdrawal lumen wall 210 extends beyond the infusion lumen tip 206. For instance, a length dimension of the withdrawal lumen wall 210 (e.g. 30 centimeters, 15 centimeters, 13 centimeters, or the like) may be greater than a length dimension of the infusion lumen wall 204 (e.g., 10 centimeters, 5 centimeters, 3 centimeters, or the like). Accordingly, the withdrawal lumen wall 210 may extend beyond the infusion lumen wall 204, for instance to longitudinally offset the withdrawal lumen tip 212 from the infusion lumen tip 206.

FIG. 2 shows the withdrawal lumen wall 210 extending beyond the infusion lumen wall 204. As discussed herein, the withdrawal lumen wall 210 may include the proximal section 218. The withdrawal lumen wall 210 may include a transition section 220. For instance, the transition section 220 of the withdrawal lumen wall 210 may extend from the proximal section 218 of the withdrawal lumen wall 210. In an example, the transition section 220 may be coupled with the proximal section 218.

The withdrawal lumen wall 210 may include a distal section 222. The distal section 222 of the withdrawal lumen wall 210 may extend from the transition section 220. For example, the distal section may be coupled with the transition section 220. The transition section 220 may facilitate a change in profile (e.g., one or more of cross-section, shape, size, dimensions, contour, radius, perimeter, circumference, diameter, outline, boundary, configuration, pattern, arrangement, thickness, or the like) of the withdrawal lumen wall 210. For instance, the transition section facilitates the change in profile between the proximal section 218 and the distal section 222 of the withdrawal lumen wall 210. In some examples, the distal section 222 includes a constant profile (e.g., constant cross-sectional area, constant diameter, or the like) with respect to a transitioning profile (e.g., changing cross-sectional area, changing diameter, or the like) of the transition section 220.

In an example, the transition section 220 of withdrawal lumen wall 210 may vary in profile with respect to a profile of the proximal section 218 of the withdrawal lumen wall 210. For instance, the proximal section 218 of the withdrawal lumen wall 210 may have a first dimension characteristic (e.g., radius, diameter, width, height, cross-sectional area, volume, or the like). The transition section 220 may have a second dimension characteristic. The second dimension characteristic may be different than the first dimension characteristic. In an example, a cross-sectional area of the transition section 220 (or a portion of the transition section 220) may be greater than a cross-sectional area of the proximal section 218. For instance, the transition section 220 may taper between the proximal section 218 and the distal section 222. Because the transition section 220 provides for a change in the dimension characteristic of the withdrawal lumen wall 210 (and the withdrawal lumen 208), the distal section 222 may have the second dimension characteristic.

In an example, the dual lumen catheter 200 includes a central axis 224. The central axis 224 may extend longitudinally along the catheter 200. For instance, the central axis may extend parallel to a longitudinal segment 226 of the withdrawal lumen wall 210. The central axis 224 may be located between the infusion lumen 202 and the withdrawal lumen 208. In another example, the central axis 224 may be located between the proximal section 216 of the infusion lumen wall 204 and the proximal section 218 of the withdrawal lumen wall 210. For instance, the proximal section 216 of the infusion lumen wall 204 may be located on a first side (e.g., top side, or the like) of the central axis 224. The proximal section 218 of the withdrawal lumen wall 210 may be located on a second side (e.g., bottom side, or the like) of the central axis 224.

As described herein, the transition section 220 of withdrawal lumen wall 210 may vary in profile with respect to a profile of the proximal section 218 of the withdrawal lumen wall 210. In an example, the transition section 220 of the withdrawal lumen wall 210 extends across the central axis 224 of the dual lumen catheter 200. For instance, the transition section 220 of the withdrawal lumen wall 210 may include a transition wall segment 228 that extends across the central axis 224. In another example, the transition wall segment 228 is located on the second side of the central axis 224. The transition wall segment 228 may extend away from the longitudinal wall segment 226. Accordingly, the transition section 220 of the withdrawal lumen wall 210 may be located on both the first side and the second side of the central axis 224. Thus, the transition section facilitates a change in profile of the withdrawal lumen wall 210 (and the withdrawal lumen 208). For example, the transition wall segment 228 extending across the central axis 224 corresponds to the change from the first dimension characteristic of the proximal section 218 to the second dimension characteristic of distal section 222.

Figure 3:
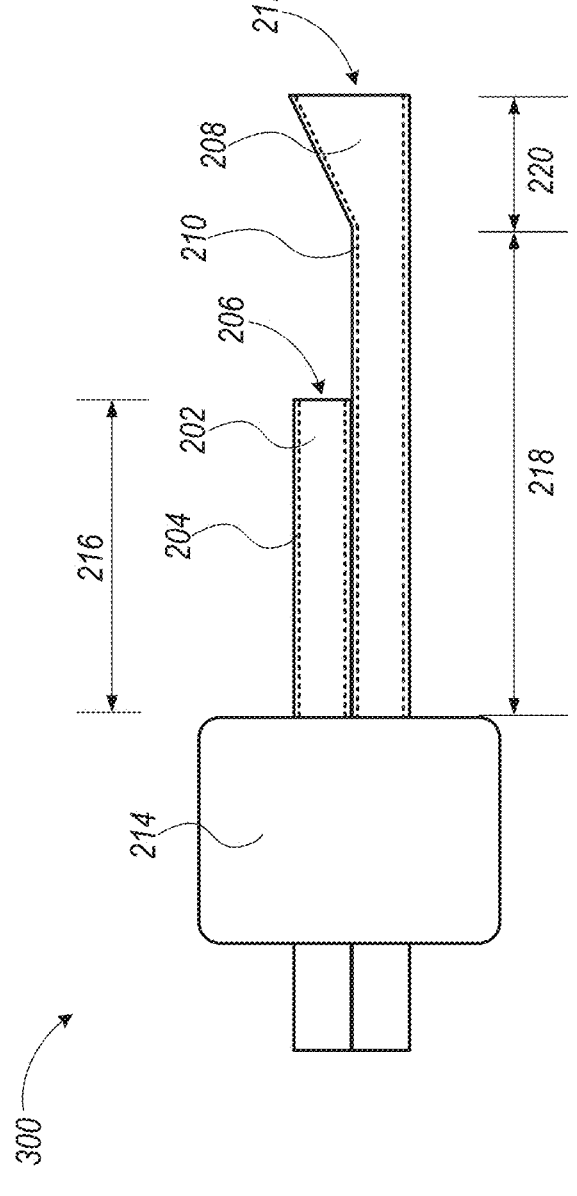
FIG. 3 shows a side view of another example of a dual lumen catheter, according to an embodiment of the present subject matter.

FIG. 3 shows another example of a dual lumen catheter 300, according to an embodiment of the present subject matter. The catheter 300 includes the infusion lumen wall 204 surrounding the infusion lumen 202. The infusion lumen wall 204 includes a proximal section 216 extending from the hub 214 to the infusion lumen tip 206. The dual lumen catheter 300 includes the withdrawal lumen wall 210 surrounding the withdrawal lumen 208. The proximal section 218 of the withdrawal lumen wall 210 extends beyond the infusion lumen wall 204 (and the infusion lumen tip 206).

The transition section 220 of the dual lumen catheter 300 includes the withdrawal lumen tip 212. For instance, the dual lumen catheter 300 (shown in FIG. 3) may not include the distal section 222 of the dual lumen catheter 200 (shown in FIG. 2). Accordingly, in some examples, the withdrawal lumen wall 210 includes the proximal section 218, and the transition section 220 having the withdrawal lumen tip 212.

Figure 4:
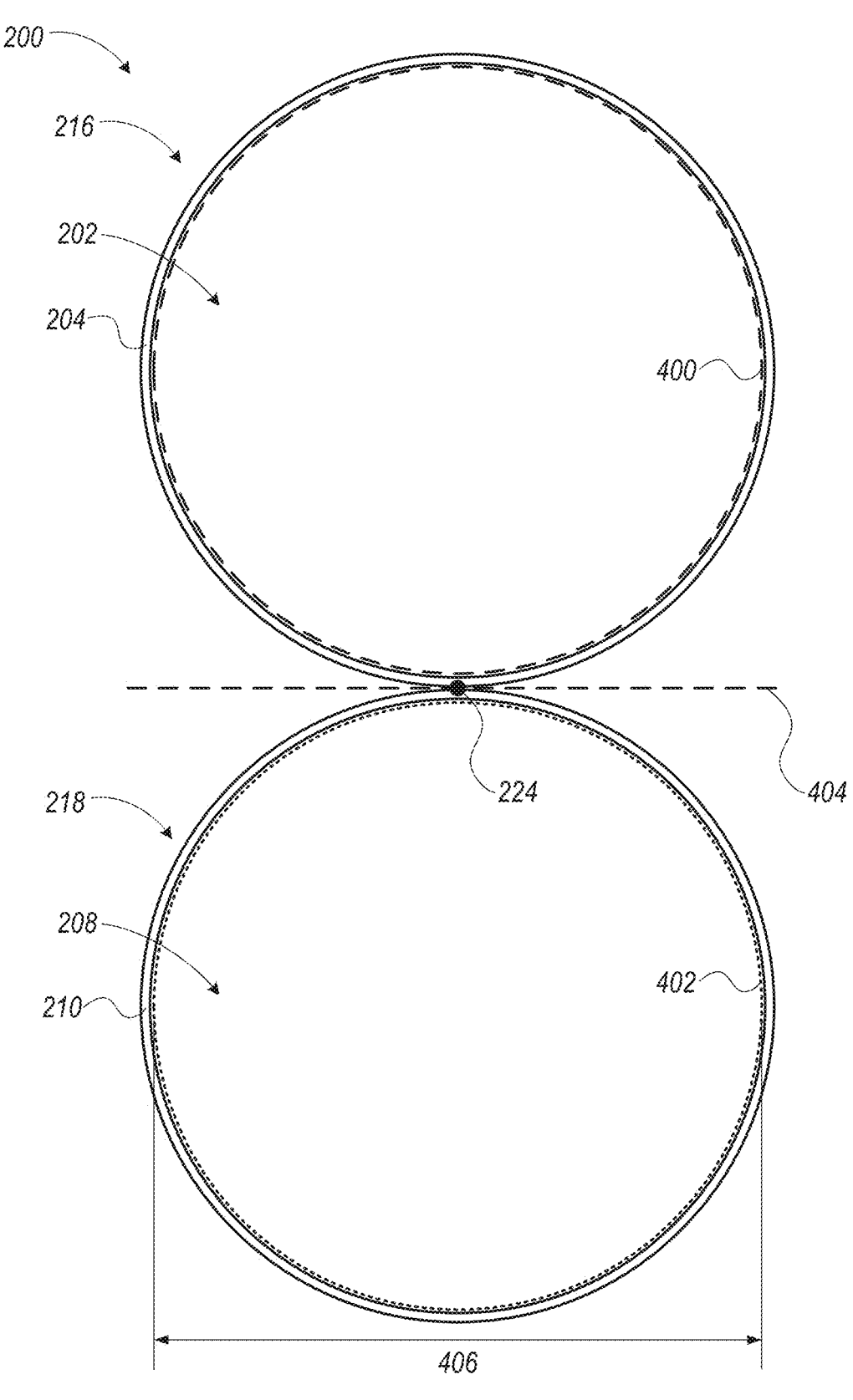
FIG. 4 shows a cross-sectional view of the dual lumen catheter of FIG. 2 at the line 4-4, according to an embodiment of the present subject matter.

FIG. 4 shows a cross-sectional view of the dual lumen catheter 200 of FIG. 2 at the line 4-4, according to an embodiment of the present subject matter. As described herein, the dual lumen catheter 200 may include the proximal section 216 of the infusion lumen wall 204 surrounding the infusion lumen 202 (also shown in FIG. 2). The catheter 200 may include the proximal section 218 of the withdrawal lumen wall 210 surrounding the withdrawal lumen 208 (also shown in FIG. 2). The central axis 224 (shown as a solid dot in FIG. 4) extends longitudinally along the dual lumen catheter 200.

Referring to FIG. 4, the infusion lumen wall 204 may include an infusion lumen profile 400 (e.g., one or more of cross-section, shape, size, dimensions, contour, radius, perimeter, circumference, diameter, outline, boundary, configuration, pattern, arrangement, thickness, or the like). The infusion lumen profile 400 may correspond to a perimeter of the infusion lumen 202. FIG. 4 shows the infusion lumen profile 400 on a first side (e.g., top side) of the central axis 224. For instance, a transverse axis 404 intersects the central axis 224. The transverse axis 404 may be offset (e.g., angled, orthogonal, perpendicular, or the like) relative to the central axis 224. The infusion lumen profile 400 may be located on a first side of the transverse axis 404.

The withdrawal lumen wall 210 may include a withdrawal lumen profile 402 (e.g., one or more of cross-section, shape, size, dimensions, contour, radius, perimeter, circumference, diameter, outline, boundary, configuration, pattern, arrangement, thickness, or the like). The withdrawal lumen profile 402 may correspond to a perimeter of the withdrawal lumen 208. FIG. 4 shows the withdrawal lumen profile 402 on a second side (e.g., bottom side) of the central axis 224. For instance, withdrawal lumen profile 402 may be located on a second side of the transverse axis 404 intersecting the central axis 224.

FIG. 4 shows the proximal section 218 of the withdrawal lumen 208 (and the profile 402) has a first dimension characteristic 406. In an example, the first dimension characteristic corresponds to a diameter of the withdrawal lumen 208. In another example, the first dimension characteristic corresponds to a width of the withdrawal lumen. In another example, the first dimension characteristic 406 corresponds to a cross-sectional area of the withdrawal lumen 208. In another example, the infusion lumen 202 (and the profile 400) has the first dimension characteristic 406.

Figure 5:
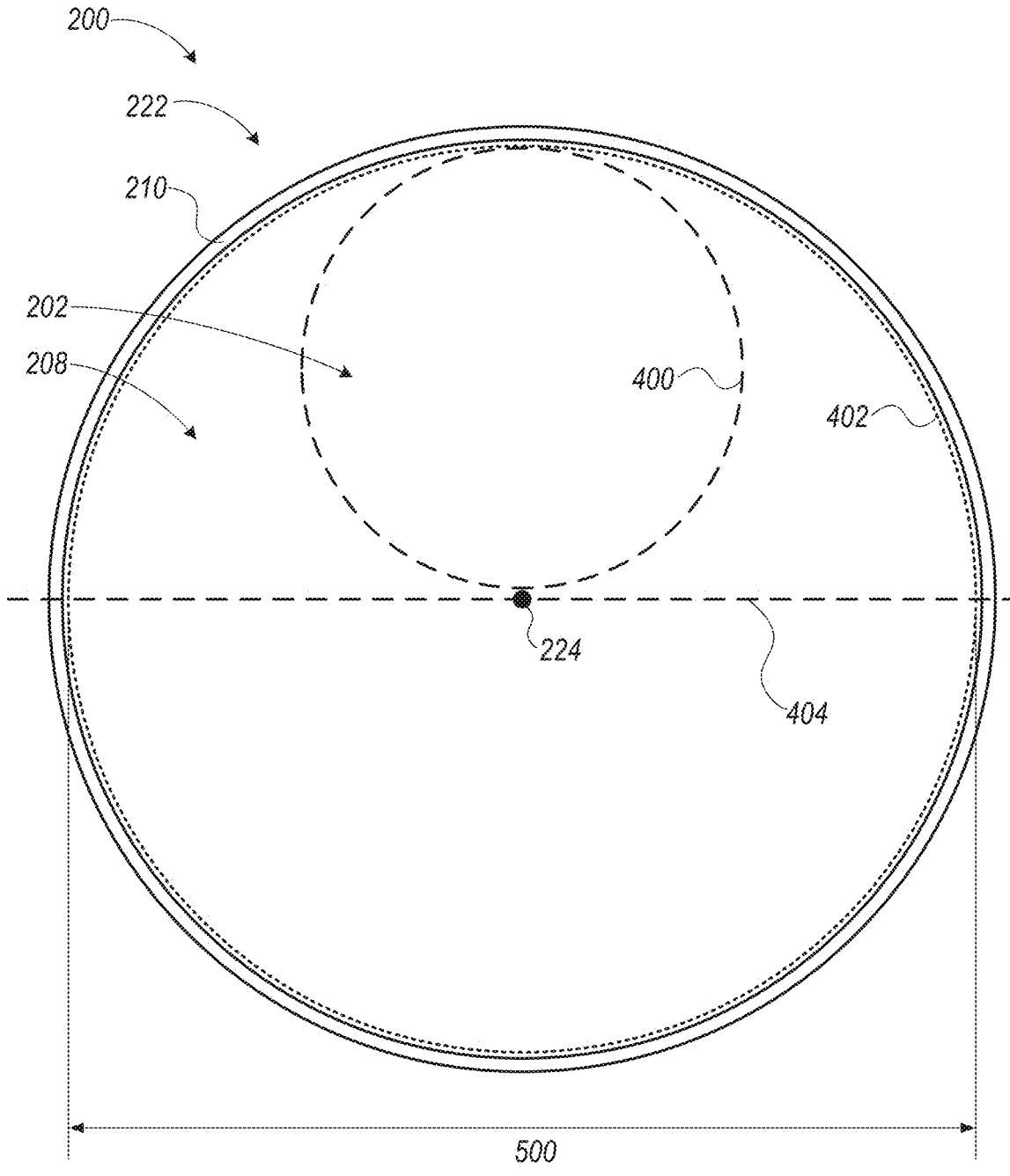
FIG. 5 shows a cross-sectional view of the dual lumen catheter of FIG. 2 at the line 5-5, according to an embodiment of the present subject matter.

FIG. 5 shows a cross-sectional view of the dual lumen catheter 200 of FIG. 2 at the line 5-5, according to an embodiment of the present subject matter. The line 5-5 is shown at the distal section 222 of the proximal section 218 of the withdrawal lumen wall 210 (shown in FIG. 2). Referring to FIG. 5, the withdrawal lumen wall 210 may surround the withdrawal lumen 208. The withdrawal lumen profile 402 may correspond to the perimeter of the withdrawal lumen wall 210. For example, the distal section 222 withdrawal lumen wall 210 has a second dimension characteristic 500. Because the transition section 220 of the withdrawal lumen wall 210 facilitates the change in profile between the proximal section 218 and the distal section 222 of the withdrawal lumen wall 210 (shown in FIG. 2), the profile of the wall 210 may vary between the first dimension characteristic 406 (shown in FIG. 4) and the second dimension characteristic 500 (shown in FIG. 5). Accordingly, the withdrawal lumen profile 402 may vary between one or more of the proximal section 218, the transition section 220, or the distal section 222 of the withdrawal lumen wall 210.

The variation in withdrawal lumen profile 402 may reduce resistance within the withdrawal lumen 208 (and the blood circuit 120). Reducing resistance may enhance flow, such as the flow of blood, with the withdrawal lumen 208. Enhancing flow within the withdrawal lumen 208 may enhance flow within the blood circuit 120. Enhancing flow within the blood circuit 120 may reduce clotting within one or more components of the blood circuit 120 (e.g., the catheter 200, the filter 110 shown in FIG. 1, or the like). In an example, the distal section 222 of the withdrawal lumen 208 may have reduced resistance to flow in comparison to the proximal section 218 of the withdrawal lumen 208. In an example, the change from the first dimension characteristic 406 in the proximal section 218 to the second dimension characteristic 500 in the transition section 220 (shown in FIG. 2) facilitates a reduction in resistance to flow through the withdrawal lumen 208.

In an example, the withdrawal lumen wall 210 extends across the central axis 224. For instance, the distal section 222 (and the transition section 220, shown in FIG. 2) of the withdrawal lumen wall 210 may extend across the central axis 224. In another example, the withdrawal lumen wall 210 extends across the transverse axis 404 intersecting central axis 224. Accordingly, the withdrawal lumen profile 402 may extend across the central axis 224 (and the transverse axis 404).

The transition section 220 extending across the central axis 224 minimizes overall dimensions of the catheter 200, for example to facilitate fluid flow within the vasculature of a patient while the catheter is located within the vasculature. In an approach, a catheter occupying space within vasculature reduces fluid flow within the vasculature. Accordingly, the overall dimensions of the catheter 200 are minimized to enhance flow within the vasculature. For instance, the transition section 220 and the distal section 222 occupy space on the first side of the central axis that is unoccupied by the infusion lumen 202 (because the withdrawal lumen wall 210 extends beyond the infusion lumen tip 206). In another example, the longitudinal offset between the infusion lumen tip 206 and the withdrawal lumen tip 212 allows the withdrawal lumen wall 210 to extend across the central axis 224. Accordingly, the withdrawal lumen 208 may transition from the first dimension characteristic 406 (shown in FIG. 4) in the proximal section 218 to the second dimension characteristic 500 (shown in FIG. 5) in the transition section 220 (and the distal section 222).

FIG. 5 shows the withdrawal lumen profile 402 in the distal section 222 of the withdrawal lumen wall 210 at least partially overlapping the infusion lumen profile 400 in the proximal section 216 of infusion lumen wall 204 (also shown in FIG. 4). The withdrawal lumen profile 402 at least partially overlaps the infusion lumen profile 400 because the transition section 220 of the withdrawal lumen wall 210 extends across the central axis 224 (and the transverse axis 404), thereby facilitating a change in the profile 402 between proximal section 218 and the distal section 222 of the withdrawal lumen wall 210. Thus, in an example, the transition from the first dimension characteristic 406 in the proximal section 216 to the second dimension characteristic 500 in the distal section 222 may correspond to the withdrawal lumen profile 402 overlapping at least a portion of the infusion lumen profile 400. The overlapping of the withdrawal lumen profile 402 with the infusion lumen profile 400 may minimize the overall dimensions of the catheter 200. Accordingly, the overlapping of the withdrawal lumen profile 402 with the infusion lumen profile 400 may facilitate minimizing overall dimensions of the catheter 200 and may enhance fluid flow within vasculature while the catheter 200 is located within the vasculature.

Figure 6:
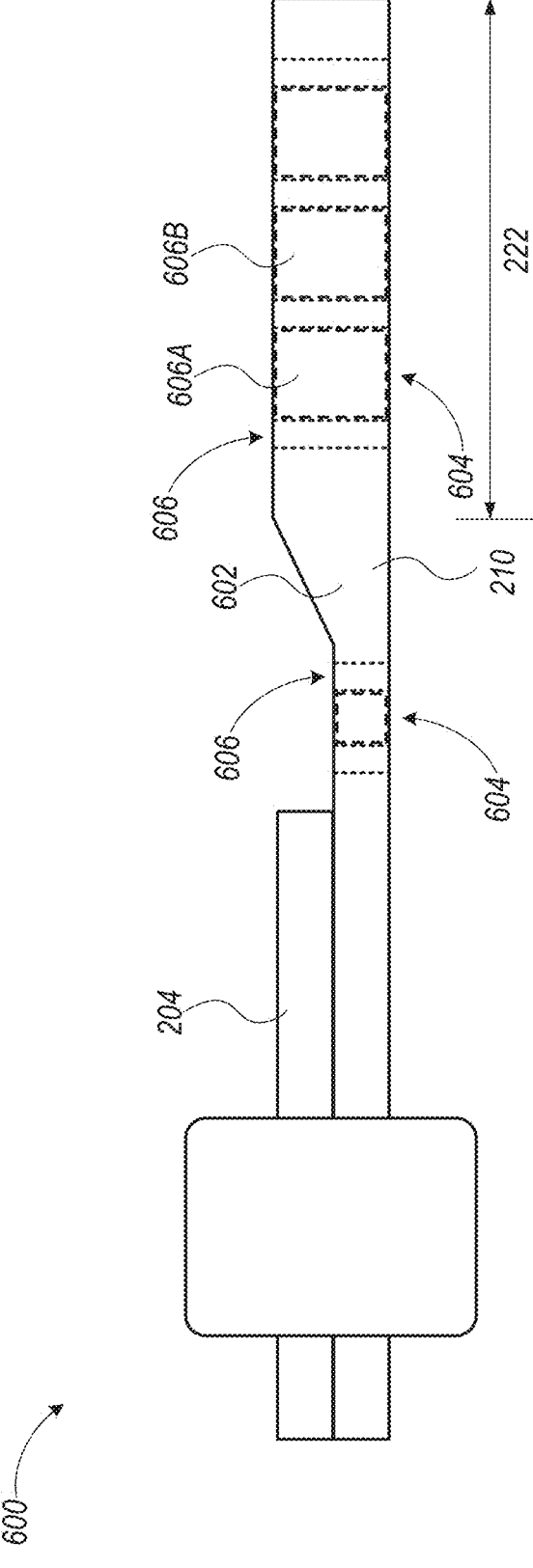
FIG. 6 shows a side view of yet another example of a dual lumen catheter.

FIG. 6 shows a side view of yet another example of a dual lumen catheter 600. The dual lumen catheter 600 may include the infusion lumen wall 204, and may include the withdrawal lumen wall 210. In an example, infusion lumen wall 204 and the withdrawal lumen wall 210 may include a polymeric material 602 (e.g., a bio-compatible plastic, or the like). The catheter 600 may include one or more structural support sections 604. For instance, the structural support sections 604 may include (but not limited to) a coil, wire, multi-filar wire, braid, weave, or the like. The structural support sections 604 may be embedded in the polymeric material 602. In an example, the structural support sections 604 may enhance the rigidity of the catheter 200. Enhancing the rigidity of the catheter may enhance the performance of the catheter 200, for instance by minimizing kinking of the withdrawal lumen wall 210 (or the infusion lumen wall 204). In another example, enhancing the rigidity of the structural support sections 604 may minimize collapse of the withdrawal lumen 208, for instance due to negative pressure applied to the withdrawal lumen 208.

In another example, the catheter 200 includes one or more trimming sections 606. The trimming sections 606 may facilitate customization of a length dimension of the catheter 200, for example customizing a length dimension of the withdrawal lumen wall 210. The trimming sections 606 may be located between the structural support sections 604 of the catheter 200. Accordingly, a user (e.g., a healthcare provider, such as a nurse or the like) may cut the polymeric material 602 at the trimming sections 606 without encountering the structural support sections 604. Thus, the structural support sections 604 enhance the rigidity of the catheter 200, and the trimming sections allow customization of the length dimension of the catheter 200.

Customization of the length dimension of the catheter 200 may enhance performance of the catheter 200 (and the blood filtration system 100), for example by allowing the withdrawal lumen tip 212 to be located in a specified location (e.g., a central vein, distal to the axillary bend, or the like). The specified location may vary between a first patient and a second patient. For instance, customizing the length dimension of the catheter 200 allows the catheter 200 to accommodate anatomic variability from patient to patient. Accordingly, the trimming sections 606 facilitate customization of the length dimension of the catheter 200 and allow the catheter 200 to be used for the first patient and the second patient. In an example, the withdrawal lumen wall 210 has a first length dimension, and the first length dimension locates the withdrawal lumen tip 212 at the specified location for the first patient. In another example, the withdrawal lumen wall 210 has a second length dimension, and the second length dimension locates the withdrawal lumen tip 212 at the specified location for the second patient.

In an example, the structural support sections 604 may be segmented by the trimming sections 606. For instance, a first structural support 604A (e.g., a first coil, or the like) may be separated from a second structural support 604B (e.g., a second coil, or the like) by a first trimming section 606A. The first trimming section 606A may include the polymeric material 602. The structural supports 604A, 604B may be embedded in the polymeric material 602 and the first structural support 604A may be separated from the second structural support 604B by the polymeric material 602. Accordingly, the trimming sections 606A does not include the structural supports 604A, 604B and a user may cut (e.g., trim, slice, chop, snip, or the like) the polymeric material 602 without encountering the structural supports 604A, 604B.

In yet another example, customizing the length of the catheter 200 may reduce recirculation of blood from the infusion lumen 202 into the withdrawal lumen 208. Recirculation includes blood that has already passed through a filter (e.g., the filter 110, shown in FIG. 1) and is drawn back into the system before fully mixing with the circulatory system of a patient. For instance, in some approaches blood flows from the infusion lumen 202 into the withdrawal lumen 208 without flowing through remaining portions of the circulatory system (e.g., the heart, or the like). Accordingly, blood that has already passed through the filter flows into withdrawal lumen and back through the blood circuit 120 (shown in FIG. 1). In some approaches, recirculation may cause the blood to become hemoconcentrated enough for clotting to occur in the blood circuit 120. Thus, customizing the length of the catheter 200 allows for the withdrawal lumen 208 to be remote from the infusion lumen 202 while accommodating anatomic variability from patient to patient.

The system 100 may include one or more components, features, functions, or the like of the subject matter discussed in PCT application PCT/US2019/069130, which is hereby incorporated by reference herein in its entirety.

For example, the blood filtration system 100 includes one or more sensors 124. In an example, FIG. 1 shows the withdrawal line 104 may be in communication with a characteristic sensor 124A. The infusion line 106 may be in communication with a characteristic sensor 124B. The sensor 124A may determine pressure in the withdrawal line 104 the sensor 124B may determine pressure in the infusion line 106. The sensors 124A, 124B may be in communication with the controller 102, and the controller 102 may monitor the pressure in the lines 104, 106 using the sensors 124A, 124B.

When the controller 102 operates the blood pump 112, the blood pump 112 generates a negative pressure in withdrawal line 104 to withdraw blood from the vasculature where the catheter tip 130 is located. The blood pump 112 may generate a positive pressure in the infusion line 106 to infuse blood into the vasculature where the catheter tip 130 is located. The magnitude of the pressure in lines 104, 106 may increase to correspondingly increase the blood flow rate within the lines 104, 106. In some examples, the magnitude of pressure in the withdrawal line 104 is approximately equal to the magnitude of pressure in the infusion line 106.

The blood circuit 120 (including the lines 104, 106) may have a total resistance characteristic that corresponds to an amount of resistance in the blood circuit 120 to the flow of blood through one or more components of the blood circuit, for instance the lines 104, 106 or the filter 110. One or more characteristics may contribute to the total resistance characteristic of the lines 104, 106. For example, the resistance characteristic of the lines 104, 106 may increase due to occlusion (e.g., clotting, obstruction, or the like) of the blood circuit 120 (e.g., in or around the catheter 108), changes to the vasculature (e.g., inflammation of walls of the vasculature, compression of the vasculature, or the like), hemoconcentration of the blood, or the like. The resistance characteristic (e.g., transverse or longitudinal) of the filter 110 may contribute to the total resistance characteristic of the blood circuit 120.

An increase in the resistance characteristic of the lines 104, 106 (or other components of the blood circuit 120) may diminish blood flow through the lines 104, 106. The resistance characteristic of the lines 104, 106 may be referred to as access resistance. The diminished blood flow due to the increase in the resistance characteristic of the lines 104, 106 may reduce the performance of the system 100, for example by reducing the maximum blood flow rate through the blood circuit 120 or the rate that the one or more blood constituents may be removed from the blood by the filter 110. The resistance characteristic of the lines 104, 106 may increase to the point where the blood pump 112 is unable to maintain flow within the lines 104, 106 (e.g., because the forces resisting flow in the lines exceeds the forces generated by the blood pump 112). Accordingly, an increase in the resistance characteristic of the lines 104, 106 may diminish the performance of the blood filtration system 100.

The system 100 may determine a total resistance characteristic for one or more components of the blood circuit 120, for example the withdrawal line 104 and the infusion line 106. In an example, a withdrawal line resistance characteristic may correspond to the resistance in the withdrawal line 104 to the flow of blood through the withdrawal line 104. The withdrawal line resistance characteristic may correspond to the pressure in the withdrawal line 104 divided by the actual blood flow rate of system 100 (e.g., as determined by a flow sensor). The actual blood flow rate of the system 100 may vary from a set point that the controller 102 operates the blood pump 112 at. For example, the resistance characteristic of the lines 104, 106 may reduce the actual blood flow rate through the blood circuit 120 because the resistance to the flow of blood in the lines 104, 106 decreases the efficiency of the blood pump 112.

The infusion line resistance characteristic may correspond to the resistance in the infusion line 106 to the flow of blood through the infusion line 106. The infusion line resistance characteristic may correspond to the pressure in the infusion line 106 divided by the difference between the actual blood flow rate and the filtration rate of the system (e.g., as determined by controller 102 in communication with the sensors 124). An increase in the magnitude of the resistance characteristic of the blood circuit 120 (including the lines 104, 106) may increase the force necessary to withdraw blood from (or infuse blood into) the patient by the blood pump 112. The increase in the magnitude of the resistance characteristic of the blood circuit 120 may result in (or be an indication of) clotting in the blood circuit 120. The blood flow stimulator may be modulated according to one or more of the characteristics of the blood circuit 120.

In yet another example, the phase of the respiratory cycle of a patient may be monitored (e.g. end inspiration, end expiration, or other phase), for example with respiratory monitor (e.g., a sensor utilizing one or more of bioimpedance plethysmography, pneumatic plethysmography, photoelectric plethysmography, pulse oximetry, strain gage plethysmography, spirometry, or the like). The force applied to the limb may be synchronized to the monitored respiratory phase (e.g., using the controller of the blood filtration system). For instance, the blood filtration system 100 may include a respiratory sensor 128 (shown in FIG. 1). The respiratory sensor 128 may determine a respiratory cycle of the patient. For instance, the respiratory sensor 128 may determine when the patient inhales or exhales (e.g., a point in time when the patient stops inhaling). The controller 102 may be in communication with the sensor 128, and the controller 102 may monitor the respiratory cycle of the patient.

Figure 7A:
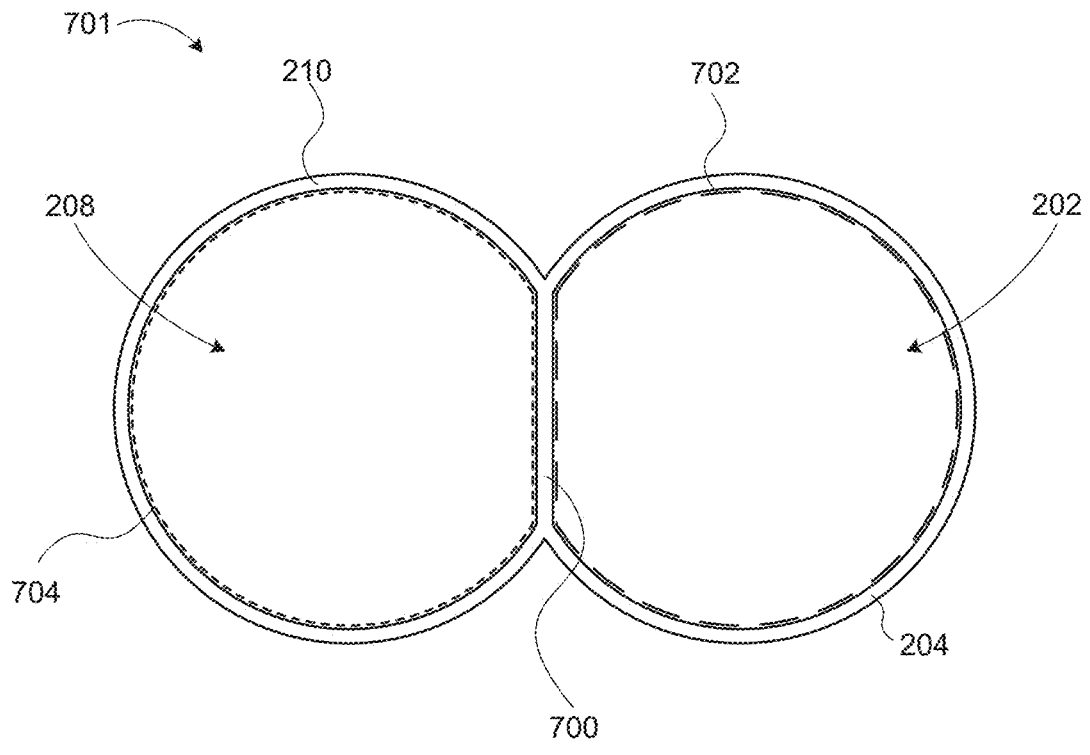
FIG. 7A show a schematic diagram of still yet another example of a dual lumen catheter.
Figure 7B:
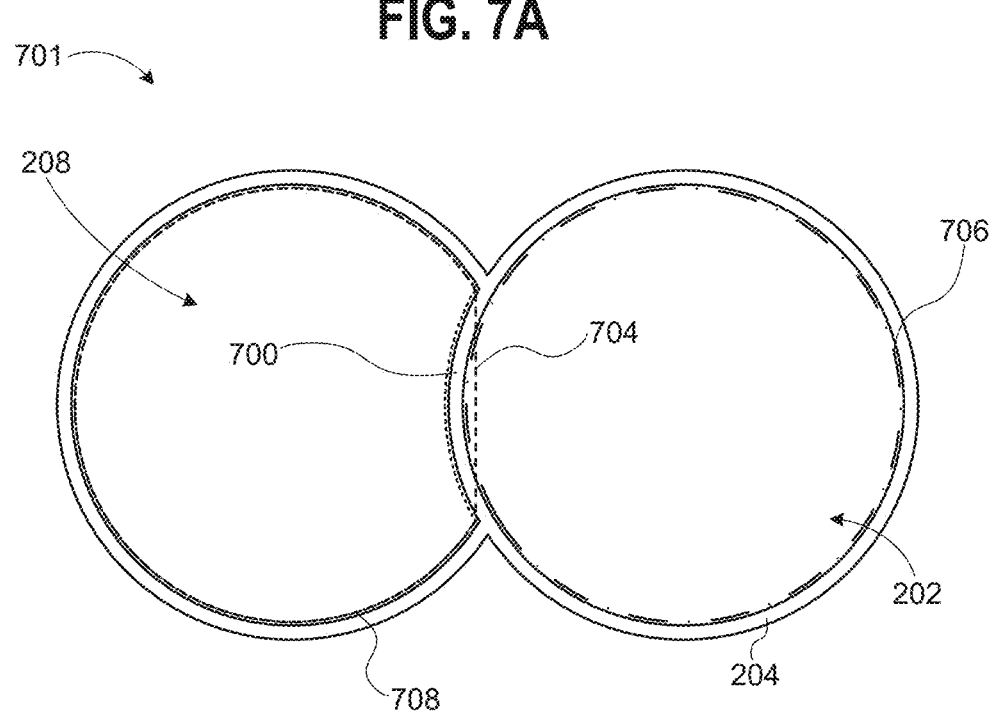
FIG. 7B shows another schematic diagram of the dual lumen catheter of FIG. 7A.

FIGS. 7A and 7B show schematic diagrams of still yet another example of a dual lumen catheter 701. In an example, the dual lumen catheter 701 includes the infusion lumen 202 surrounded by the infusion lumen wall 204, and the withdrawal lumen 208 surrounded by the withdrawal lumen wall 210. The infusion lumen 202 has an infusion lumen profile 702. The withdrawal lumen 208 has a withdrawal lumen profile 704. In some examples, a flexible septum 700 is located between the infusion lumen 202 and the withdrawal lumen 208. The flexible septum 700 may isolate the infusion lumen 202 from the withdrawal lumen 208.

In an approach, the infusion lumen profile 702 is equal to (or larger than) the withdrawal lumen profile 704. In this approach, the septum 700 may deflect toward the withdrawal lumen 208. For instance, the blood pump 112 (shown in FIG. 1) generates a negative pressure in the withdrawal lumen 208 to draw blood into the withdrawal lumen 208. The blood pump 112 drives the blood through other components of the blood circuit 120 (shown in FIG. 1). For instance, the blood pump 112 drives blood through the filter 110 and into the infusion lumen 202. In an example, the blood pump 112 generates a positive pressure in the infusion lumen 202, for instance to pump blood back into vasculature.

In some approaches, and as shown in FIG. 7B, the pressure differential generated by the blood pump 112 between the withdrawal lumen 207 and the infusion lumen 202 causes deflection of the septum 700 into the withdrawal lumen 208. The deflection of the septum 700 (shown in FIG. 7B) into the withdrawal lumen 208 may reduce the withdrawal lumen profile 704 (in comparison to the withdrawal lumen profile 704 shown in FIG. 7A). In this approach, the deflection of the septum 700 into the withdrawal lumen 208 (shown in FIG. 7B) reduces flow through the withdrawal lumen 208. For instance, the deflection of the septum 700 into the withdrawal lumen 208 reduces the cross-sectional area of the withdrawal lumen 208. Accordingly, the flow rate through the withdrawal lumen 208 is reduced when the septum 700 is deflected toward the withdrawal lumen because the septum 700 reduces the cross-sectional area of the withdrawal lumen 208. In another example, the deflection of the septum toward the withdrawal lumen 208 increases the resistance to flow within the withdrawal lumen 208. Accordingly, minimizing deflection of the septum 700 toward the withdrawal lumen 208 enhances performance of the catheter 700, for instance by maintaining the cross-sectional area of the withdrawal lumen 208 during operation of the blood pump 112 (shown in FIG. 1). Thus, obstruction of blood flow in the withdrawal lumen is minimized with the catheter 700.

In some approaches, blood flow is reduced between the catheter and other components of the blood filtration system 100. For instance, the blood may stagnate within the blood circuit 120. The reduction in blood flow through the components may cause the blood to clot within the components of the blood filtration system 100 (e.g., the blood circuit 120, the filter, or the like). For example, blood may clot within the components of the blood filtration system due to blood stasis within the components. Thus, the components may be replaced to resume operation of the blood filtration system 100. Accordingly, reducing blood statis within the components enhances performance of the blood filtration system 100 by reducing clotting. In an example, reducing clotting of components of the blood filtration system 100 reduces replacement of the components during therapy of a patient.

Figure 8:
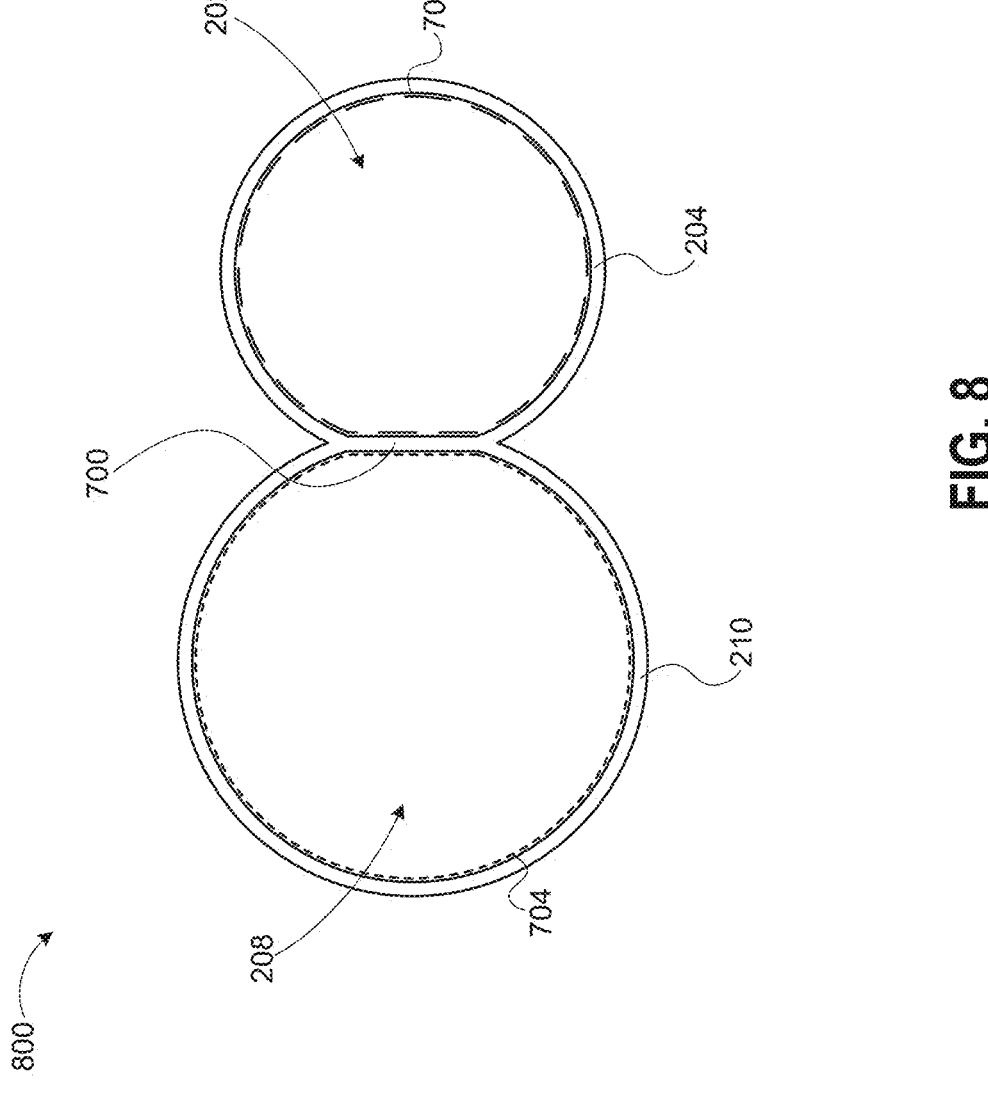
FIG. 8 shows a schematic diagram of a further example of a dual lumen catheter.

FIG. 8 shows a schematic diagram of a further example of a dual lumen catheter 800. In an example, the withdrawal lumen profile 704 is larger than the infusion lumen profile 702. For instance, FIG. 8 shows the withdrawal lumen 208 having a greater cross-sectional area than the infusion lumen 202. In an example, the cross-sectional area of the infusion lumen 202 may be at least 10 percent smaller than the cross-sectional area of the withdrawal lumen 208 (however the present subject matter is not so limited). In this example, the difference between the infusion lumen profile 702 and the withdrawal lumen profile 704 increases blood velocity in the infusion lumen 202 (in comparison to the blood velocity in the withdrawal lumen). For example, the velocity of blood flow increases in the infusion lumen 202 due to continuity between the infusion lumen 202 and the withdrawal lumen 208. In another example, the difference between the infusion lumen profile 702 and the withdrawal lumen profile 704 decreases blood velocity in the withdrawal lumen 208 (in comparison to the blood velocity in the infusion lumen 202).

In yet another example, an increase in blood velocity within a lumen correspondingly increases the dynamic pressure within the lumen. For instance, the dynamic pressure in the infusion lumen 202 is greater than the dynamic pressure in the withdrawal lumen 208. The increase in blood velocity within the lumen may correspondingly decrease the pressure against a wall of the lumen (e.g., the septum 700, the infusion lumen wall 204, or the like). Accordingly, the septum 700 is inhibited from deflection toward the withdrawal lumen 208 (and correspondingly reducing flow within the withdrawal lumen 208). Thus, blood flow within the withdrawal lumen 208 is enhanced because the infusion lumen profile 702 is smaller than the withdrawal lumen profile 704.

In still yet another example, the increase in blood velocity within the lumen generates a force imbalance upon the septum 700 toward the infusion lumen 202 (instead of the withdrawal lumen 208. For instance, the difference between the infusion lumen profile 202 and the withdrawal lumen profile 208 causes a force imbalance that deflects the septum 700 toward the infusion lumen 202. For example, Equation 1 shows the total pressure (Ptotal) within a lumen is equal to the sum of the dynamic pressure (Pd) and the transmural pressure (Pw).

$$Ptotal = Pw + Pd \qquad \text{Equation 1:}$$

Equation 2 (e.g., Bernoulli's equation, or the like) shows that the total pressure in the withdrawal lumen 208 (Ptotal1) is based (in part) on the velocity of fluid in the withdrawal lumen 208:

$$Ptotal1 = Pw1 + 0.5 * \rho * (v1)^2 \qquad \text{Equation 2:}$$

Equation 3 (e.g., Bernoulli's equation, or the like) shows that the total pressure in the infusion lumen 202 (Ptotal2) is based (in part) on the velocity of fluid in the infusion lumen 202:

$$Ptotal2 = Pw2 + 0.5 * \rho * (v2)^2 \qquad \text{Equation 3:}$$

Equation 4 (e.g., the Continuity Equation) shows that the rate of mass (e.g., blood, or the like) entering the withdrawal lumen 208 (corresponding to the velocity of fluid times the area of the withdrawal lumen 208) is equal to the rate of mass exiting the infusion lumen 202 (corresponding to the velocity of fluid times the area of the infusion lumen 202):

$$v1 * A1 = v2 * A2 \qquad \text{Equation 4: v}$$

Equation 4 shows the velocity of blood in the withdrawal lumen 208 multiplied by the cross-sectional area of the withdrawal lumen 208, is equal to the velocity of blood in the infusion lumen 202 multiplied by the cross-sectional area of the infusion lumen 202. In an example where the cross-section of the withdrawal lumen 208 and the infusion lumen 202 is circular in shape, Equation 4 may be algebraically manipulated to yield Equation 5:

$$v2 = v1 * \left(\frac{r1}{r2}\right)^2 \qquad \text{Equation 5}$$

Equation 6 assumes the total pressure in the infusion lumen 202 is equal to the pressure in the withdrawal lumen 208. Accordingly, Equation 6 is equivalent to Equation 2 equaling Equation 3:

$$Pw1 + 0.5 * \rho * (v1)^2 = Pw2 + 0.5 * \rho * (v2)^2 \qquad \text{Equation 6:}$$

Substituting equation 5 into Equation 6, and performing algebraic manipulation yields Equation 7. In Equation 7, r1 corresponds to the radius of the withdrawal lumen 208 and r2 corresponds to the radius of the infusion lumen 202:

$$Pw2 = Pw1 + 0.5 * \rho * v1^2 * \left[1 - \left(\frac{r1}{r2}\right)^4\right] \qquad \text{Equation 7}$$

Accordingly, the transmural pressure (against the septum) within the withdrawal lumen 208 is greater than the transmural pressure within the infusion lumen 202. The difference in transmural pressure inhibits deflection of the septum 700 toward the withdrawal lumen 208 and instead deflects the septum 700 toward the infusion lumen 202. Thus, the resistance to blood flow within the withdrawal lumen 208 is minimized, and performance of the blood filtration system 100 is enhanced by reducing stagnation (or stasis) of blood within components of the blood circuit 120.

Figure 9:
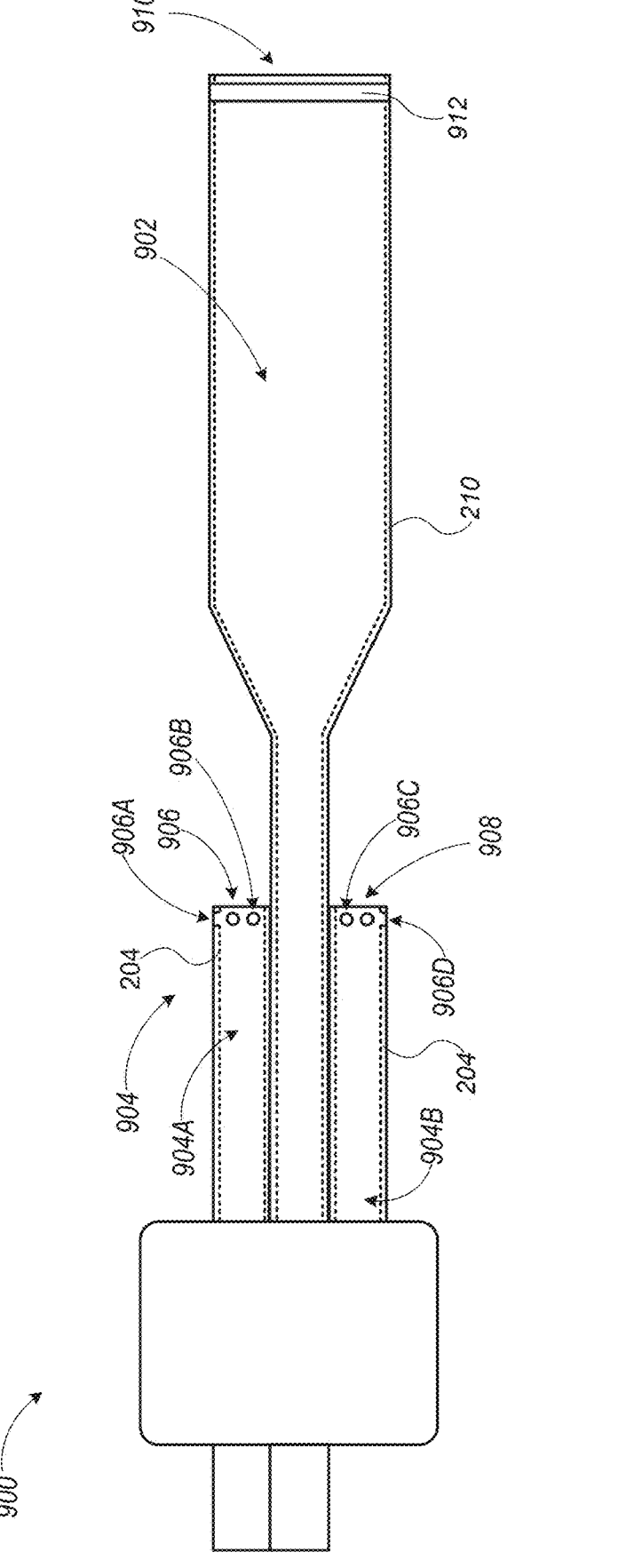
FIG. 9 shows a schematic diagram of yet another example of a multi-lumen catheter.

FIG. 9 shows a schematic diagram of yet another example of a multi-lumen catheter 900. In an example, the multi-lumen catheter 900 includes a withdrawal lumen 902. The multi-lumen catheter 900 may include a plurality of infusion lumens 904. For instance, the multi-lumen catheter 900 includes a first infusion lumen 904A and a second infusion lumen 904B. The lumens 904A, 904B may be inserted into vasculature, and infuse blood into a patient. For instance, the hub 214 may distribute blood from the infusion line 106 to the lumens 904A, 904B. The blood may flow through the lumens 902A, 902B for infusion into the vasculature of the patient.

The plurality of infusion lumens 904 may stabilize the catheter within vasculature of the patient. For instance, the plurality of infusion lumens 904 may balance forces generated from blood emerging from the multi-lumen catheter 900. In an example, the infusion lumen 904A may be on a first side (e.g., top side, or the like) of the withdrawal lumen 902. The infusion lumen 904B may be on a second side (e.g., bottom side, or the like) of the withdrawal lumen 902. In another example, the infusion lumen 904A may be radially offset from infusion lumen 904B. For example, the infusion lumen 904A may be offset by 180 degrees about the withdrawal lumen 904 from the infusion lumen 904B. Accordingly, forces generated by blood emerging from the infusion lumen 902A may be offset by forces generated from blood emerging from the infusion lumen 902B.

In some approaches, tip whipping of the catheter 900 may occur, wherein the blood emerging from the catheter causes the (intracorporeal) catheter 900 to move back and forth within the vein lumen. Tip whipping may reduce blood flow in the vein (leading to a reduction in available blood to enter the withdrawal lumen 904). Accordingly, balancing forces generated by blood emerging from the catheter 900 may reduce tip whipping, and enhance performance of the blood filtration system 100. In an example, the plurality of infusion lumens 904 balance forces about the withdrawal lumen 902 to stabilize the catheter 900 within the vein (e.g., by reducing tip whipping, or the like) and enhance the available blood flow for the blood filtration system 100 (shown in FIG. 1).

In another example, the infusion lumens 904 include one or more apertures 906 extending through the infusion lumen wall 204 of the infusion lumens 904. The apertures 906 enhance the performance of the catheter 900 by stabilizing the catheter 900 within the vein). For instance, the first infusion lumen 904A may include one or more of a first aperture 906A or a second aperture 906B extending through the infusion lumen wall 204 of the first infusion lumen 904A. In yet another example, the second infusion lumen 904B may include one or more of a third aperture 906C or a fourth aperture extending through the infusion lumen wall 204 of the second infusion lumen 904B. The apertures 906 may enhance stability of the catheter 900 within the vein lumen, for instance by balancing forces acting upon the catheter 900 within the vein lumen.

In still yet another example, the apertures 906 allow blood to emerge from the infusion lumens 904 if a portion of the infusion lumens 904 are occluded. For instance, the plurality of apertures 906 may allow blood (or other fluid) to flow from the infusion line 106 (shown in FIG. 1) into the vein lumen even if a portion the catheter 900 is eccentrically located within the vein lumen. For example, the apertures 906 may allow blood to flow from the infusion lumen 904B with a tip 908 of the infusion lumen 904B occluded (e.g., blood flow is inhibited from exiting the tip 908 due to engagement with a vein wall, or the like). Accordingly, apertures 906 may enhance performance of the catheter 900 by allowing blood to flow from the infusion lumens 904 if the tip 908 is occluded (or if individual ones of the apertures 906 are occluded).

Referring to FIG. 9, the catheter 900 may include a catheter tip 910 (e.g., a tip of the withdrawal lumen 902, or the like) having a magnetic sleeve 912 embedded in the catheter 900. In another example, the magnetic sleeve 912 may have a different magnetic response in comparison to the remainder of the catheter tip 910. For example, the magnetic sleeve 912 may be embedded in the withdrawal lumen wall 210. The magnetic sleeve 912 may enhance locating the catheter tip 910 while inserting the catheter 900 into vasculature of a patient. For instance, an external dongle may detect the magnetic sleeve 912 when the dongle is located proximate to the magnetic sleeve 912 Accordingly, a healthcare provider may know that the dongle is proximate the catheter tip 910.

Figure 10:
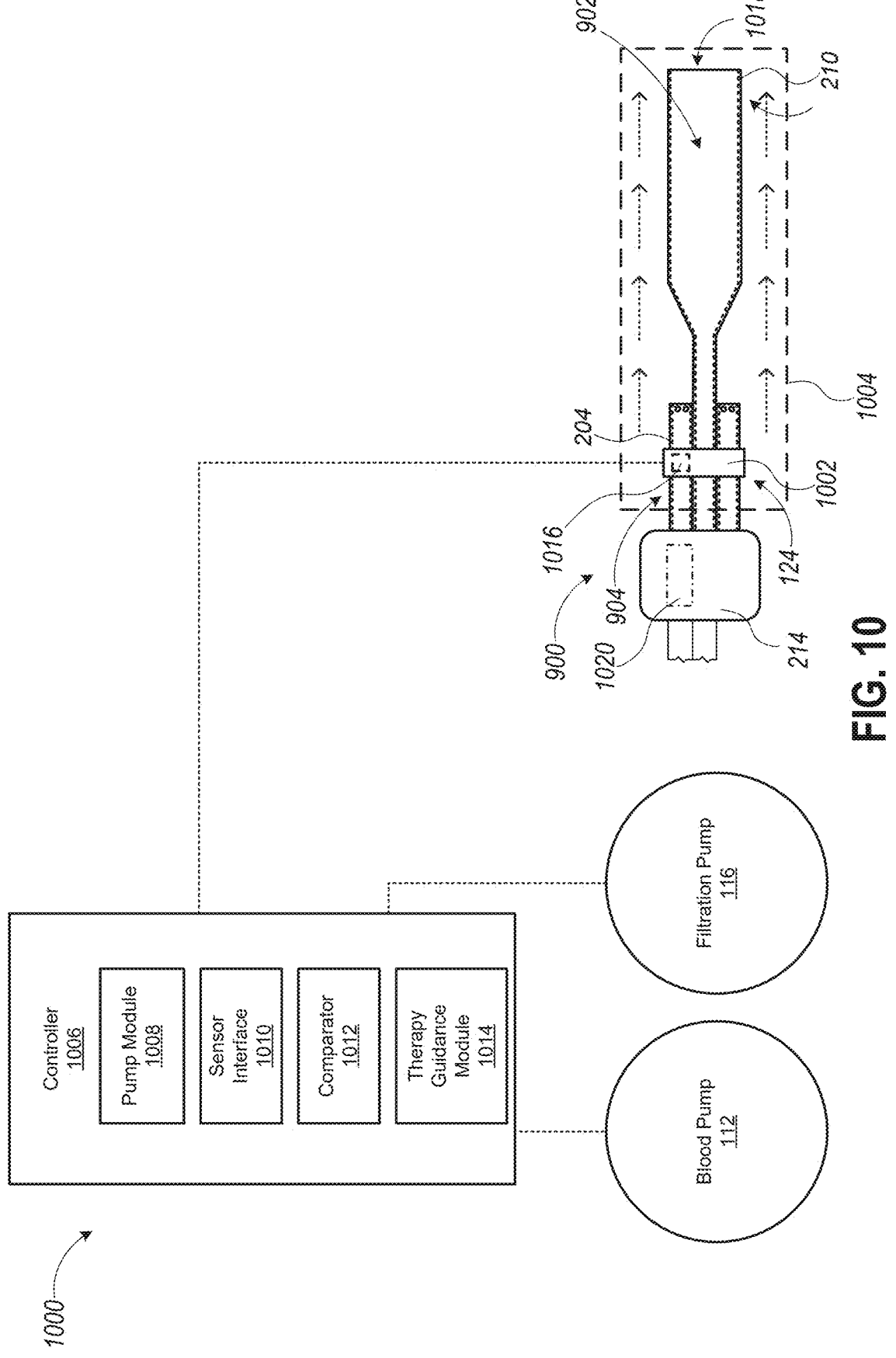
FIG. 10 shows a schematic diagram of another example of a blood filtration system.

FIG. 10 shows a schematic diagram of another example of a blood filtration system 1000. The blood filtration system 1000 may include the blood filtration system 100. For instance, the blood filtration system 1000 may include one or more components, features, or functions (or the like) of the blood filtration system 100. The blood filtration system 1000 monitors venous blood flow rate in vasculature where the catheter 108 is located. For instance, the catheter 108 may be inserted into a basilic vein of a patient, and the blood filtration system 1000 may monitor the blood flow rate of blood flowing through the basilic vein where the catheter is inserted. In another example, the system 1000 includes the catheter 900.

In some approaches, blood filtration (e.g., including, but not limited to, veno-venous extracorporeal therapies, or the like) may be challenging because the rate at which the blood pump 112 drives blood through the blood circuit 120 is greater than the natural venous flow rate in the vasculature where a catheter for the blood circuit 120 is inserted. In this approach, the blood pump may stop operating, and accordingly the blood filtration system may provide a notification to alert a healthcare provider that the blood pump 112 stopped operating. In another approach, a withdrawal pressure may be measured to determine venous flow rate.

The blood filtration system 1000 may monitor venous blood flow rate and vary the speed one or more of the blood pump 112 or the filtration pump 116 based on the monitored venous blood flow rate. For example, the blood filtration system 1000 may maintain the speed of the blood pump 112 to refrain from withdrawing blood from a vein at a rate that exceeds the monitored blood flow rate in the vein. In another example, the blood flow rate in the vein varies with respect to time. For instance, the blood flow rate in the vein varies based on respiration of the patient, movement of the patient, or the like. Accordingly, the blood filtration system may monitor the blood flow rate in a vein to minimize cessation of flow of blood in the blood circuit 120 by varying the speed of the blood pump 112 based on the monitored blood flow rate in the vein where the catheter (e.g., the catheter 900, or the like) is inserted.

In an example, the catheter 108 may include a blood flow sensor 1002. The blood flow sensor 1002 determines one or more of a velocity of blood flowing through a vein or the flow rate of blood in the vein. For instance, the blood flow sensor 1002 determine the velocity (or flow rate) of blood flowing between catheter 108 and a wall of the vein 1004. In an example, FIG. 10 includes dashed arrows showing the flow of blood within the vein 1004. FIG. 10 shows blood flowing around the catheter 108 within the vein 1004. The blood flow sensor 1002 may determine the velocity (or flow rate) of the blood flowing around the catheter 108 within the vein 1004.

In another example, the blood filtration system 1000 includes a controller 1006. The controller 1006 may include the controller 102 (shown in FIG. 1). For instance, the controller 1006 may include one or more features, functions, instructions, algorithms, configurations, or the like that are included in the controller 102. In another example, the controller 1006 may include a pump module 1008. The pump module 1008 operates the pumps 112, 116 of the blood filtration system 1000. For example, the pump module 1008 operates one or more of the blood pump 112 or the filtration pump 116 during therapy for a patient.

In yet another example, the controller 1006 may include a sensor interface 1010. The sensor interface may facilitate communication of the controller with sensors of the blood filtration system 1000. For example, the sensor interface 1010 facilitates communication with the one or more sensors 124 (also shown in FIG. 1). In another example, the one or more sensors 124 include the blood flow sensor 1002. Accordingly, the blood flow sensor 1002 may communicate with the controller 1006 using the sensor interface 1010.

As described herein, the blood filtration system 1000 monitors venous blood flow rate and varies the speed one or more of the blood pump 112 or the filtration pump 116 based on the monitored venous blood flow rate. In an example, the controller 1006 monitors the blood flow rate (or velocity of blood) in the vein 1004 using the blood flow sensor 1002. For instance, the controller 1006 may use the sensor interface 1010 to receive the blood flow rate determined by the blood flow sensor 1002. In another example, the controller 1006 may vary a speed of one or more of the blood pump 112 or the filtration pump 116 based on the monitored blood flow rate through the vein 1004. Accordingly, the controller 1006 may vary a flow rate of one or more of the blood pump 112 or the filtration pump 116 based on the monitored flow rate through the vein 1004.

For example, the controller 1006 determines a flow rate of the blood pump 112. The controller 1006 may use the pump module 1008 to determine the flow rate of the pump 112 based on the speed of the blood pump 112. The controller 1006 may operate the blood pump 112 to limit the flow rate of the blood pump 112 to a limit less than the monitored blood flow rate through the vein 1004. For instance, the controller 1006 may operate the blood pump 112 within a range of blood flow rates. The controller 1006 may use the monitored blood flow rate through the vein 1004 as a threshold flow rate and limit the flow rate of the blood pump 112 to be lower than the threshold flow rate (optionally corresponding to the monitored blood flow rate through the vein 1004). In another example, the therapy guidance module 1014 may guide the flow rate through the blood circuit toward a specified blood circuit flow rate. For instance, the therapy guidance module 1014 may guide the monitored blood flow rate to the specified blood circuit flow rate. In an example, the therapy guidance module may determine an error between the monitored blood flow rate and the specified blood circuit flow rate. The therapy guidance module 1014 may cooperate with the pump module 1008, for instance to reduce the error between the monitored blood flow rate and the specified blood circuit flow rate. Accordingly, the therapy guidance module 1014 may guide the monitored flow rate toward the specified blood circuit flow rate.

In an example, the controller 1006 may include a comparator 1012 that compares the flow rate of the blood pump 112 to the monitored blood flow rate through the vein 1004. The controller 1006 may change operation of the blood pump 112 based on the comparison of the flow rate of the blood pump 112 to the monitored blood flow rate through the vein 1004.

In another example, the controller 1006 may include a therapy guidance module 1014 to enhance operation of the blood filtration system 1000. The therapy guidance module 1014 may guide one or more of the flow rate or the extraction rate based on flow through the vein 1004. For instance, the therapy guidance module 1014 may monitor the speed of the pumps 112, 116 (or flow rates through the pumps 112, 116). The therapy guidance module 1014 may monitor the blood flow rate through the vein 1004 and cooperate with the pump module 1008 to change the speed of the pumps 112, 116 based on the monitored blood flow rate through the vein 1004. For example, the therapy guidance module 1014 may reduce the speed (and flow rate) of the blood pump 112 based on a decrease in the monitored blood flow rate through the vein 1004. In another example, the therapy guidance module 1014 increases the speed (and flow rate) of the blood pump 112 based on an increase in the monitored blood flow rate through the vein 1004.

In yet another example, the pump module 1008 determines a flow rate of the filtration pump 116 that may extract filtrate fluid from a filter. The controller 1006 changes operation of the filtration pump 116 based on the monitored blood flow rate through the vein 1004. In an example, the therapy guidance module 1014 reduces a speed of the filtration pump 116 based on a decrease in the blood flow rate through the vein 1004. In another example, the therapy guidance module 1014 increases a speed of the filtration pump 116 based on an increase in the blood flow rate through the vein 1004. In another example, the therapy guidance module 1014 changes the operation of the pumps 112, 116 in proportion to the monitored blood flow rate through the vein 1004.

Referring to FIG. 10, the blood flow sensor 1002 may include an ultrasonic transducer 1016 that uses ultrasonic waves to determine the velocity of the blood in the vein 1004 (shown in FIG. 10 with arrows indicating the direction of flow through the vein 1004). For example, the ultrasonic transducer 1016 may measure the velocity of the blood in the vein 1004 that flows around the catheter 900 within the vein 1004. In another example, the ultrasonic transducer measures the velocity of the blood in the vein between the lumens 902, 904 and a wall of the vein 1004.

The catheter 900 may include the ultrasonic transducer 1016 coupled to an exterior of the catheter 900. For instance, the ultrasonic transducer may be coupled to the walls 204 of the infusion lumens 904. In another example, the ultrasonic transducer may be coupled to the wall 210 of the withdrawal lumen 902. In yet another example, blood flow sensor 1002 may be distal to the hub 214. For instance, the blood flow sensor 1002 may be located between the hub 214 and a distal tip 1018 of the withdrawal lumen 902. Accordingly, in an example, the blood flow sensor 1002 measures the flow rate of blood in the vein prior to the blood entering the withdrawal lumen 902.

FIG. 10 shows the hub 214. The hub 214 may include a signal processing module 1020. The signal processing module 1020 may convert signals generated (or received) with the ultrasonic transducer 1016. The signal processing module 1020 may be in communication with the controller 1006. For instance, the sensor interface 1010 of the controller 1006 may communicate with the signal processing module 1020 of the hub 214. In an example, the signals received by the transducer 1016 are small, high frequency (MHz) signals. The signals received by the transducer may be attenuated (or otherwise affected) by external noise signals. Accordingly, in an approach, noise signals could distort the ultimate blood velocity measurement with the ultrasonic transducer 1016. The signal processing module 1020 enhances the performance of the system 100 by processing the signals received by the ultrasonic transducer 1016. For instance, the signal processing module 1020 reduces attenuation of the signal received by the transducer 1016. Thus, the signal processing module 1020 minimizes effects of noise on the signal received by the transducer 1016.

The signal processing module 1020 may transmit the processed signals to the controller 1006. In an example, the signal processing module 1020 may convert high frequency electronics signals generated (or received) by the ultrasonic transducer 1016 into a baseband signal (e.g., a lower frequency signal that is less susceptible to interference and less likely to be attenuated). In another example, the signal processing module 1020 may convert the signal received by the ultrasonic transducer into a data stream (as opposed to analog signals). The signal processing module 1020 may transmit the data stream to the controller 1006. In some examples, the system 1000 displays the measured velocity in the vein 1004 on a display (e.g., an LCD screen, or the like).

Figure 11:
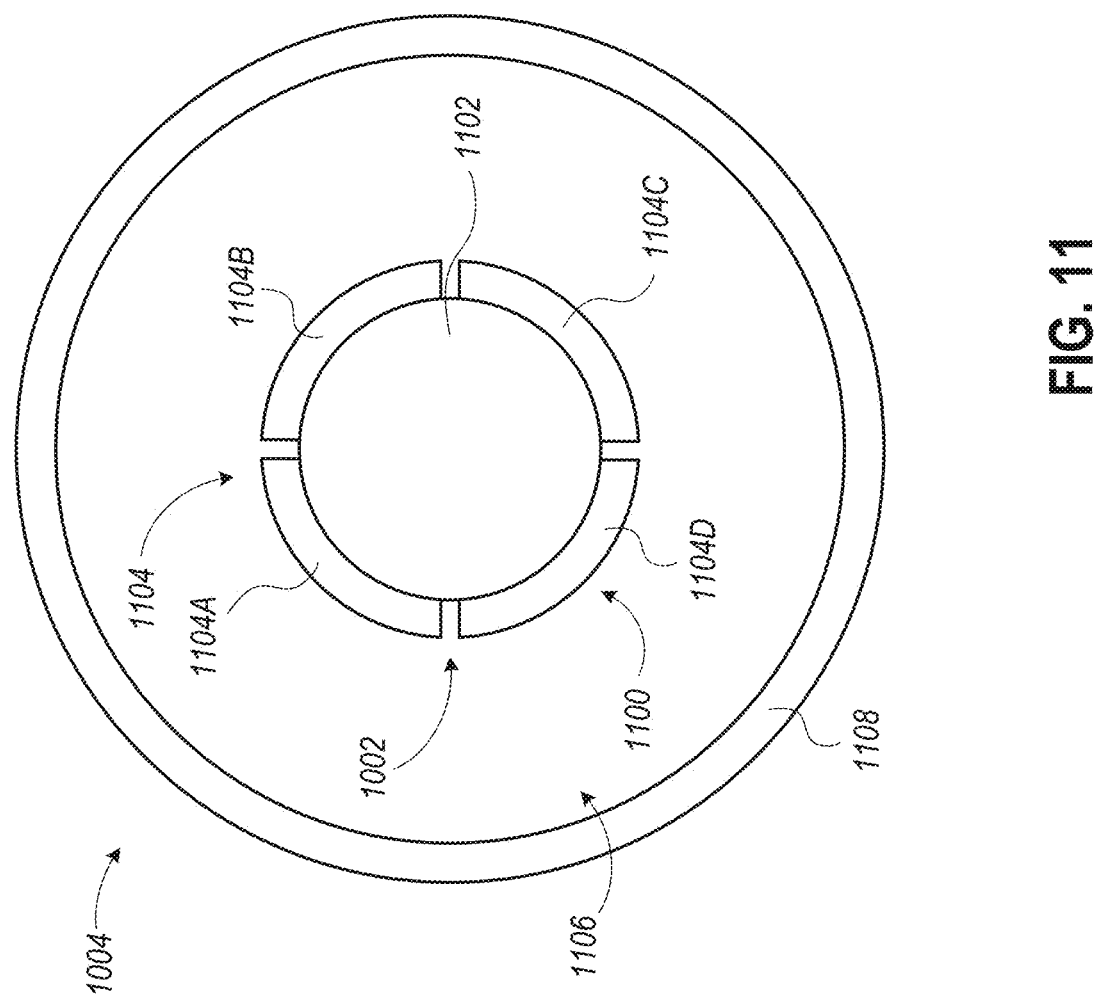
FIG. 11 shows a cross-sectional view of a catheter inserted into a vein of a patient

FIG. 11 shows a cross-sectional view of a catheter 1100 inserted into the vein 1004 of the patient. In an example, the catheter 1100 includes a catheter shaft 1102. For instance, the catheter shaft 1102 includes one or more of the withdrawal lumen 208 or the infusion lumen 202. The catheter 1100 may include the blood flow sensor 1002. In another example, the blood flow sensor 1002 includes a plurality of ultrasonic transducers 1104. For example, the plurality of ultrasonic transducers 1104 includes two or more a first ultrasonic transducer 1104A, a second ultrasonic transducer 1104B, a third ultrasonic transducer 1104C, or a fourth ultrasonic transducer 1104D. The ultrasonic sensors 1104 may be coupled to an exterior of the catheter shaft 1102.

In an example, the ultrasonic transducers 1104 facilitate determining the velocity of blood flowing in a vein lumen 1106 surrounded by a vein wall 1108 of the vein 1004. The catheter 1100 may be inserted into the vein lumen 1106. The ultrasonic transducers 1104 may determine the velocity of blood flowing between the catheter shaft 1102 and the vein wall 1108. In an example, the ultrasonic transducers 1104 transmit (and receive) ultrasonic waves that interact with the blood (e.g., red blood cells in the blood, or the like) to determine the velocity of blood in the vein lumen 1106.

Figure 12:
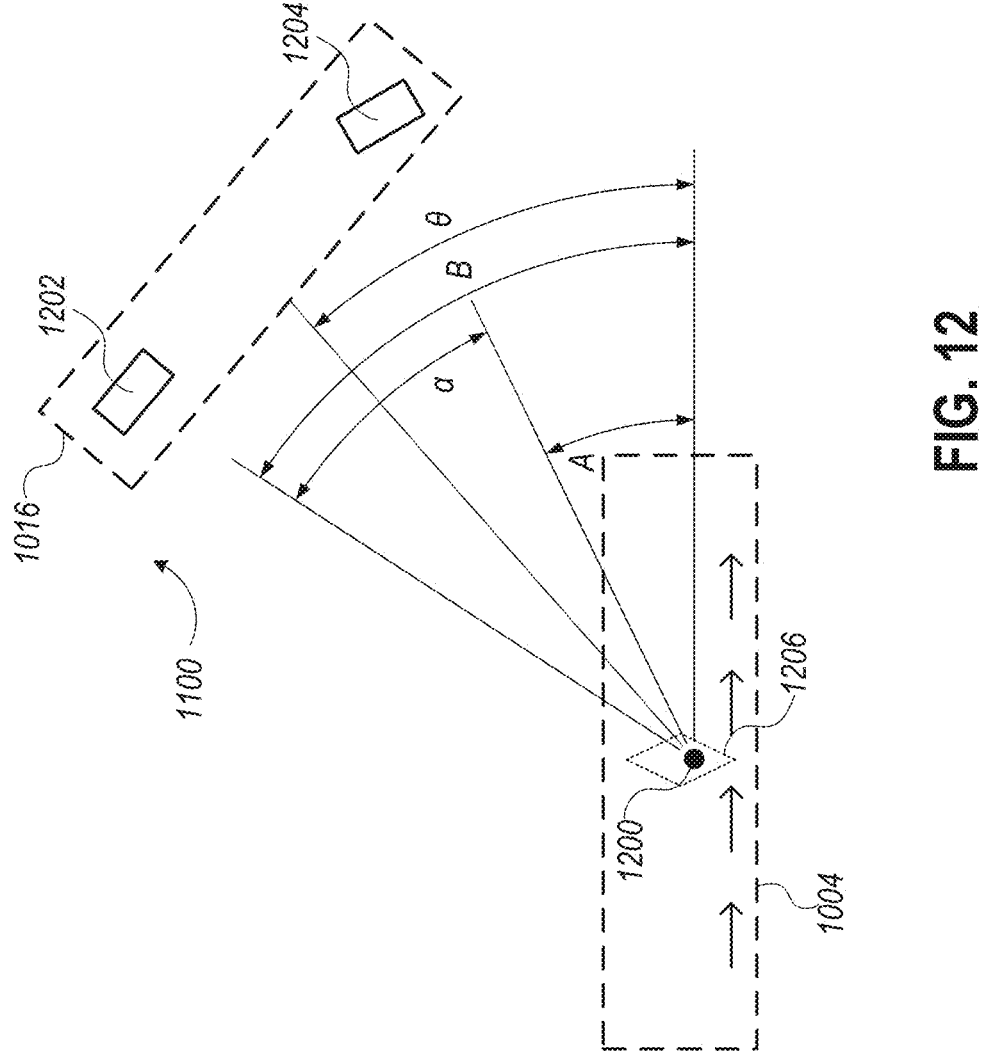
FIG. 12 shows a schematic diagram of an ultrasonic transducer.

FIG. 12 shows a schematic diagram of an ultrasonic transducer, for instance the ultrasonic transducer 1016. The ultrasonic transducer 1016 facilitates determining the velocity of blood in the vein 1004 (shown in FIG. 10). For instance, a red blood cell 1200 is a constituent of blood in the vein 1004. FIG. 10 shows the direction of movement for the red blood cell 1200 through the vein 1004 with dashed arrows. The red blood cell 1200 scatters waves generated by the ultrasonic transducer 1016, and the ultrasonic transducer determines the velocity of the red blood cell 1200 (flowing in the blood) based on the scattering of the waves by the red blood cell 1200.

In an example, the ultrasonic transducer 1016 includes a transmitter 1202 and a receiver 1204. The transmitter 1202 may generate a signal, for instance an ultrasonic wave, and the transmitter 1202 transmits the signal through the blood in the vein 1004 (shown in FIG. 10). The signal is scattered by constituents of the blood, for instance the red blood cell 1200. The scattered signal may be received by the receiver 1204. The ultrasonic transducer 1016 may determine the velocity of the red blood cell 1200 using the scattered signal received by the receiver 1204.

For example, the velocity of the red blood cell 1200 flowing through the vein 1004 may be determined according to the following equations including the variables: velocity of the red blood cell 1200 (v), speed of sound in blood (c), the frequency of the signal transmitted by the transmitter 1202 ($f_o$), the Doppler shifted frequency of the signal transmitted by the transmitter 1202 (f'), the angle between a longitudinal axis of the vein 1004 and the transducer direction ($\Theta$), and The Doppler shift frequency ($f_d$) is equal to the difference between $f_o$ and f'. Equation 8 is the Doppler shift equation and includes the following variables: the velocity of sound ($V_c$), velocity of observer ($V_{ob}$), and the velocity of source of emitted sound waves ($V_s$).

$$f' = f_o \left[ \frac{v_c \pm v_{ob}}{v_c \mp v_s} \right] \qquad \text{Equation 8}$$

Applying Equation 8 to the ultrasonic transducer 1016 and the red blood cell 1200 (shown in FIG. 12) yields Equation 9:

$$f' = f_o \left[ \frac{c - v\cos A}{c + v\cos B} \right] \qquad \text{Equation 9}$$

Equations 10 and 11 relate angles A, B, θ, and α:

$$A = \theta - \frac{\alpha}{2} \qquad \text{Equation 10}$$

-continued $$B = \theta - \frac{\alpha}{2} \qquad \text{Equation 11}$$

Substituting Equations 10 and 11 into Equation 9 yields Equation 12:

$$f' = f_o \left[ \frac{c - v\cos\left(\theta - \frac{\alpha}{2}\right)}{c + v\cos\left(\theta + \frac{\alpha}{2}\right)} \right] \qquad \text{Equation 12}$$

As described herein, the Doppler shift frequency ($f_d$) is equal to the difference between $f_o$ and f':

$$f_d = f' - f_o \qquad \text{Equation 13:}$$

Substituting Equation 12 into Equation 13 yields Equation 14:

$$f_d = f_o \left[ \frac{c - v\cos\left(\theta - \frac{\alpha}{2}\right) - c - v\cos\left(\theta + \frac{\alpha}{2}\right)}{c + v\cos\left(\theta + \frac{\alpha}{2}\right)} \right] \qquad \text{Equation 14}$$

Algebraically manipulating Equation 14 yields Equation 15:

$$f_d = f_o(-v) \left[ \frac{\cos\left(\theta + \frac{\alpha}{2}\right) + \cos\left(\theta - \frac{\alpha}{2}\right)}{c + v\cos\left(\theta + \frac{\alpha}{2}\right)} \right] \qquad \text{Equation 15}$$

Equation 15 may be algebraically manipulated to yield Equation 16:

$$f_d = \left[ \frac{-2 f_o v}{c} \right] \left[ \frac{\cos(\theta)\cos\left(\frac{\alpha}{2}\right)}{1 + \frac{v}{c}\cos\left(\theta + \frac{\alpha}{2}\right)} \right] \qquad \text{Equation 16}$$

Algebraically manipulating Equation 16 yields Equation 17:

$$|f_d| \cong \left[ \frac{2 f_o v}{c} \right] \left[ \cos(\theta)\cos\left(\frac{\alpha}{2}\right) \right] \qquad \text{Equation 17}$$

Assuming α is a small value in Equation 17 yields Equation 18:

$$|f_d| \cong \left[ \frac{2 f_o v}{c} \right] [\cos(\theta)] \qquad \text{Equation 18}$$

Equation 18 may be algebraically manipulated to determine the velocity of the red blood cell 1200 (v) in Equation 19:

$$v \cong \frac{|f_d| c}{2 f_o [\cos\theta]} \qquad \text{Equation 19}$$

Referring to FIG. 12, the ultrasonic transducer 1016 may measure the velocity of blood within a focal zone 1206. In an example, the focal zone 1206 may correspond with a region where emitted and reflected ultrasonic signals coincide with each other. For instance, the focal zone 1206 may be located within the vein 1004. In another example, the focal zone 1206 may be proximate a center of the vein 1004. In yet another example, the focal zone 1206 may be remote from walls of the vein 1004. In still yet another example, the focal length 1206 may be remote from a catheter inserted into the vein 1004. Accordingly, the velocity of the red blood cell 1200 may be detected in correspondence with the red blood cell 1200 located in the focal zone 1206.

Figure 13A:
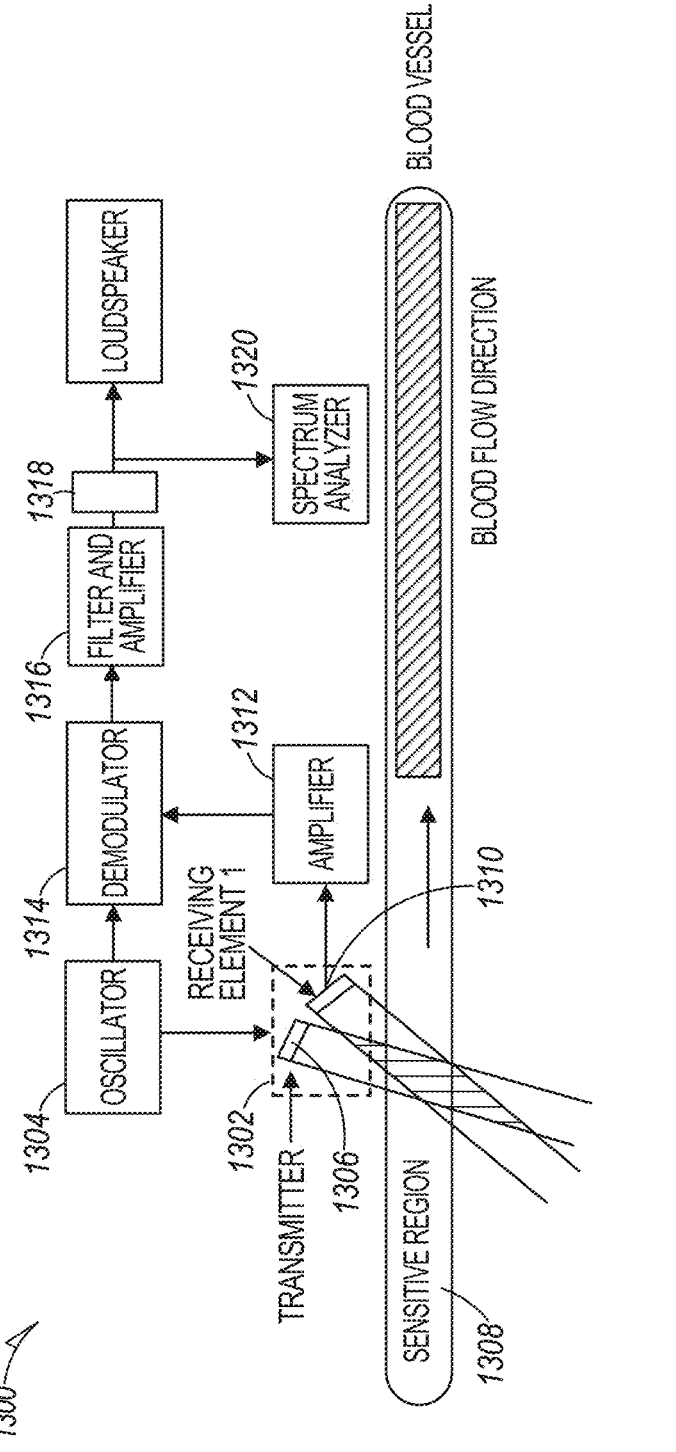
FIG. 13A shows a schematic diagram of a blood filtration system including a non-directional (or unidirectional) Doppler transducer.

FIG. 13A shows a schematic diagram of a blood filtration system 1300 including a non-directional (or unidirectional) Doppler transducer 1302. In an example, oscillator 1305 drives a transmitter 1306 to transmit ultrasonic waves that interact with blood (e.g., red blood cells in the blood, or the like) in vasculature 1308 (e.g., the vein 1004 shown in FIG. 10, an artery, or the like). For instance, the transmitter 1306 transmits ultrasonic waves to determine the velocity of blood in the vasculature 1308.

The non-directional Doppler transducer 1302 includes a receiver 1310. The receiver 1310 may receive scattered ultrasonic waves that interact with blood (e.g., the red blood cell 1200 shown in FIG. 12, or the like). The receiver 1310 may communicate the received signals to a first amplifier 1312. The amplifier 1312 may be in communication with a demodulator 1314. The demodulator 1314 may communicate with the oscillator 1304 and the amplifier 1312 to demodulate the signals received at the receiver 1310.

The system 1300 may transmit the demodulated signal to one or more of a filter 1316 or a second amplifier 1318. For instance, the second amplifier 1318 may amplify the demodulated signal that has passed through the filter 1316. In an example, the demodulated signal may be analyzed with a spectrum analyzer 1320, for instance to determine the Doppler shift frequency. In yet another example, the system 1300 uses the non-directional Doppler transducer 1302 to distinguish between flow in a vein (e.g., blood flowing in a first portion of vasculature in a first direction, or the like) and flow in an artery (e.g., blood flowing in a second portion of vasculature in a second direction). For example, the system 1300 may monitor the DC offset of the demodulated signal (e.g., with the spectrum analyzer 1320, or the like) to determine the flow rate through the vein (e.g., vasculature 1308, or the like). In another example, the system 1300 may monitor the time varying component of the demodulated signal to determine the flow rate through the artery. Accordingly, the system 1300 is able to determine if the non-directional Doppler transducer 1302 has insonated one or more of a vein or an artery. Thus, performance of the system 1300 may be enhanced by enhancing the accuracy of measured flow in the vasculature 1308 of a patient.

Figure 13B:
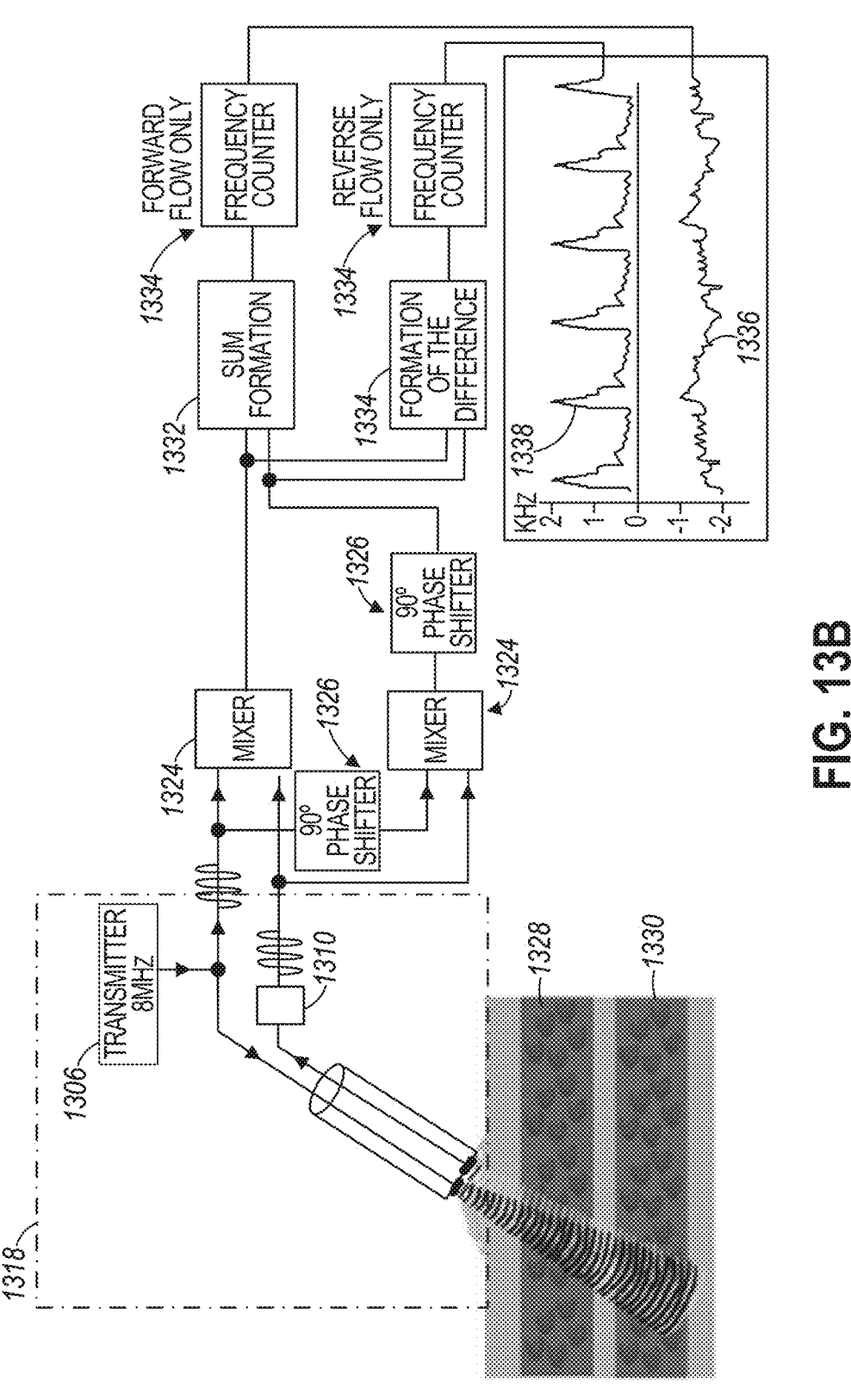
FIG. 13B shows a schematic diagram of another example of the blood filtration system including a directional (e.g., bi-directional) Doppler transducer.

FIG. 13B shows a schematic diagram of another example of the blood filtration system 1300 including a directional (e.g., bi-directional) Doppler transducer 1322. The directional Doppler transducer 1322 may include the transmitter 1306 and the receiver 1310. The receiver 1310 may transmit a signal corresponding to the received ultrasonic waves to one or more mixers 1324. In another example, the receiver 1310 may transmit the signal corresponding to the received ultrasonic waves to one or more phase shifters 1326. The mixers 1324 and the phase shifters 1326 may cooperate to condition the signal received from the receiver 1310. For example, the mixers 1324 and phase shifters 1326 may cooperate to condition received signals to determine the velocity of flow in the vasculature 1308 of the patient.

In another example, the system 1300 may use the directional Doppler transducer 1322 to distinguish between flow in a vein 1328 and flow in an artery 1330. In an example, the artery 1330 is proximate the vein 1328. Accordingly, in some examples, the directional Doppler transducer 1322 insonates both the vein 1328 and the artery 1330. The insonation of both the vein 1328 and the artery 1330 attenuates the ultrasonic waves, and the receiver 1310 receives the attenuated ultrasonic waves. Accordingly, the receiver 1310 receives a signal corresponding to flow in both the vein 1328 and the artery 1330. Thus, the system 1300 uses the directional Doppler transducer 1322 to distinguish between the flow in the vein 1328 and the flow in the artery 1330.

For example, the system 1300 uses a summation block 1332 to determine the sum (e.g., using mathematical addition, or the like) of conditioned signals that were received at the receiver 1310. The system 1300 may communicate the sum to one or more frequency counters 1334. For instance, the frequency counters 1334 may determine a vein flow signal 1336 corresponding to the flow in the vein 1328 (shown with an arrow in a first direction in FIG. 13B). The sum of the conditioned signals may correspond to flow in the vein 1328.

In another example, the system 1300 uses a difference block to determine the difference (e.g., using mathematical subtraction, or the like) between the conditioned signals that were received at the receiver 1310. The system 1300 may communicate the difference to the frequency counters 1334. For instance the frequency counters 1334 may determine an artery flow signal 1338 corresponding to the flow in the artery 1330 (shown with an arrow in a second direction in FIG. 13B). The difference between the conditioned signals may correspond to flow in the artery 1330. Accordingly, the system 1300 uses the directional Doppler transducer 1322 to distinguish between flow in the vein 1328 and flow in the artery 1330. Thus, accuracy and precision of venous flow rate determinations are enhanced because the system 1300 may distinguish between flow in the vein 1328 and flow in the artery 1330.

Figure 14:
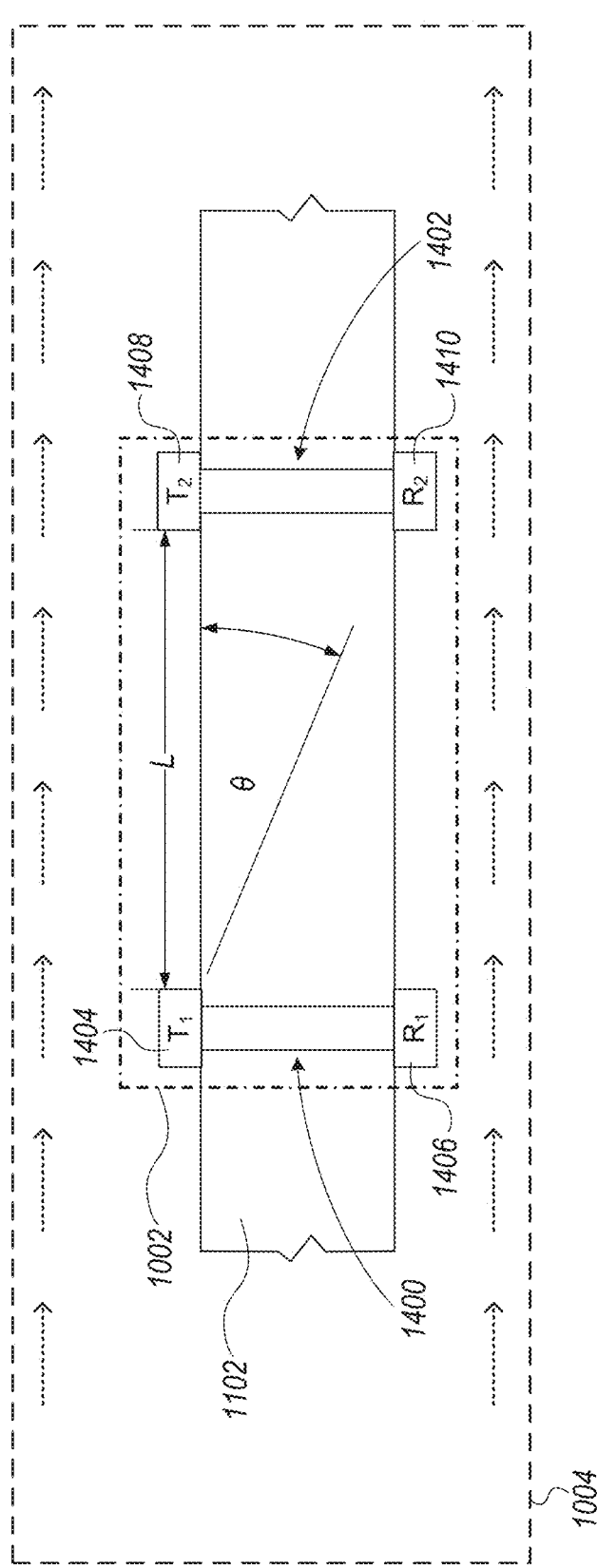
FIG. 14 shows a schematic diagram of another example of a blood flow sensor.

FIG. 14 shows a schematic diagram of another example of the blood flow sensor 1002. In an example, the blood flow sensor 1002 includes one or more of a first transducer 1400 and a second transducer 1402. The transducers 1400, 1402 may generate (and receive) ultrasonic signals. The transducers 1400, 1402 may be coupled to the catheter shaft 1102. For instance, the transducers 1400, 1402 may extend around the catheter shaft 1102. In another example, the transducers 1400, 1402 are annular in shape (e.g., ring-shaped, circular, or the like). Accordingly, the transducers 1400, 1402 may surround the catheter shaft 1102.

In an example, the blood flow sensor 1002 determines the velocity of blood flowing in the vein lumen 1106 between the catheter shaft 1102 and the wall 1108 of the vein 1004 (shown in FIG. 11). In still yet another example, the blood flow sensor 1002 determines the velocity of blood flowing through one or more components of the blood circuit 120. For instance, the blood flow sensor 1002 may determine the velocity of blood flowing through the catheter shaft 1102. In another example, the blood flow sensor 1002 determines the velocity of blood flowing through one or more of a withdrawal lumen (e.g., the withdrawal lumen 902, shown in FIG. 9) or an infusion lumen (e.g., the infusion lumens 202, shown in FIG. 2).

The first transducer 1400 may include a first transmitter 1404 and a first receiver 1406. The second transducer 1402 may include a second transmitter 1408 and a second receiver 1410. The first transducer 1400 may be located proximal to the second transducer 1402. For instance, the first transmitter 1404 may transmit a signal (e.g., including but not limited to an acoustic signal, such as an ultrasonic signal, or the like) to the second receiver 1410. The second transmitter 1408 may transmit a signal to the first receiver 1406. Accordingly, the first transducer 1400 is in communication with the second transducer 1400 to transmit and receive signals between the first transducers 1400 and the second transducer 1402.

In an example, the blood flow sensor 1002 cooperates with the controller 1006 to determine the velocity of blood flowing in the vein 1004 using the transducers 1400, 1402. For instance, the transducers 1400, 1402 may communicate to determine the velocity of blood flowing (shown with dashed arrows in FIG. 14) in the vein 1004. In another example, the blood flow sensor 1002 determines the velocity of blood flowing in the vein 1004 based on the transit time of a signal transmitted between the transducers 1400, 1402.

The blood flow sensor 1002 may transmit signals between the transducers 1400, 1402 to determine the velocity of blood. For example, the blood flow sensor 1002 may determine a first transit time ($T_{12}$) of a signal to travel from the first transmitter 1404 to the second receiver 1410. In another example, the blood flow sensor 1002 may determine the transit time ($T_{21}$) of a signal to travel from the second transmitter 1408 to the first receiver 1406. In an example, the blood flow sensor 1002 determines a difference (if any) between the first transit time $T_{12}$ and the second transit time $T_{21}$. The blood flow sensor 1002 may be in communication with the comparator 1012 (shown in FIG. 10). In another example, the controller 1006 may receive the transit times $T_{12}$, $T_{21}$, and the controller 1006 may determine a difference between the transit times $T_{12}$, $T_{21}$. The controller 1006 may use the transit times (or difference between transit times) to determine the velocity of blood flowing in the vein 1004 (or components of the blood circuit 120).

In an example, the velocity of blood flowing through the vein 1004 may be determined according to Equations 11 through 15. Equations 11 through 15 include one or more of the following variables: the first transit time (Ti 2) and the second transit time ($T_{21}$), the difference between the first transit time and the second transit time ($\Delta T$). distance between the first transducer 1400 and the second transducer 1402 (L), and the angle ($\Theta$) between the blood flow direction and a line drawn from the first transmitter 1404 to the second receiver 1410, the velocity of the signal (e.g., ultrasound, or the like) in blood (c), and blood flow velocity (v).

Equation 11 may be used to determine the first transit time $T_{12}$:

$$T_{12} = \frac{L}{c + v * \cos(\theta)} \qquad \text{Equation 11}$$

Equation 12 may be used to determine the second transit time $T_{21}$:

$$T_{21} = \frac{L}{c - v * \cos(\theta)} \qquad \text{Equation 12}$$

Equation 13 includes the difference between the second transit time and the first transit time:

$$\Delta T = T_{21} - T_{12} = \left(\frac{L}{c}\right) * \left[\frac{1}{1 - \left(\frac{v}{c}\right) * \cos(\theta)} - \frac{1}{1 + \left(\frac{v}{c}\right) * \cos(\theta)}\right] \qquad \text{Equation 13}$$

Equation 13 may be algebraically manipulated to obtain Equation 14:

$$\Delta T = 2 * \left(\frac{L}{c^2}\right) * (v) * \cos(\theta) \qquad \text{Equation 14}$$

Equation 14 may be algebraically manipulated to obtain Equation 15:

$$v = \frac{c^2 * \Delta T}{2 * L * \cos(\theta)} \qquad \text{Equation 15}$$

In an example, the controller 1006 uses one or more of Equations 11 through to determine the velocity of blood flow in the vein 1004 (or a portion of the blood circuit 120). For instance, the controller 1006 may receive the determined velocity of blood flow in the vein 1004 from the blood flow sensor 1002. In another example, the controller 1006 cooperates with the blood flow sensor 1002 to determine the velocity of blood flow in the vein 1004.

In another example, the blood flow sensor 1002 may couple with a cuvette. The blood flow sensor 1002 may measure the blood flow rate through the cuvette. For instance, the blood flow sensor 1002 may generate a signal emitted from the first transducer 1400 to the second transducer 1402 and across a lumen of a cuvette to measure the blood flow rate through the lumen of the cuvette.

For example, the controller 1006 (shown in FIG. 10) may determine the flow rate (Q) within the blood circuit based on the determined velocity of blood flowing through the blood circuit. For instance, the cuvette has an internal diameter (d). Accordingly, the flow rate through the cuvette is equal to the velocity of blood in flowing in the cuvette multiplied by the cross-sectional area of the cuvette (e.g., based on continuity, or the like).

The controller 1006 may use the determined flow rate (or velocity of flow) through components of the blood circuit (e.g., a cuvette, or the like) to facilitate correction of flow rate related artifacts in the system 1000. In one example, the blood filtration system 1000 may determine the blood flow rate through one or more portions of the blood circuit 120. For instance, the controller 1006 may determine the blood flow rate in order to correct for flow rate related artifacts in measurements conducted by the blood filtration system 1000. For example, the controller 1006 may determine a hematocrit value of blood in the blood circuit 120. In an example, the controller 1006 may communicate with a hematocrit sensor 126 (shown in FIG. 1) to determine the hematocrit value of blood in the blood circuit 120. The determined hematocrit value may vary according to blood flow rate through the blood circuit 120. For example, the hematocrit value may vary according to blood flow rate through the blood circuit 120. For example, the hematocrit value may vary according to the speed of the blood pump 112 (or flow rate through the blood circuit 120). The controller 1006 may monitor the flow rate through components of the blood circuit 120 to compensate for changes in flow rate when determining the hematocrit value of blood in the components of the blood circuit 120. Accordingly, the controller 1006 may monitor the flow rate and determine the hematocrit value at a (consistent) specified flow rate to reduce flow related artifacts in measurements conducted by the blood filtration system 1000.

Figure 15:
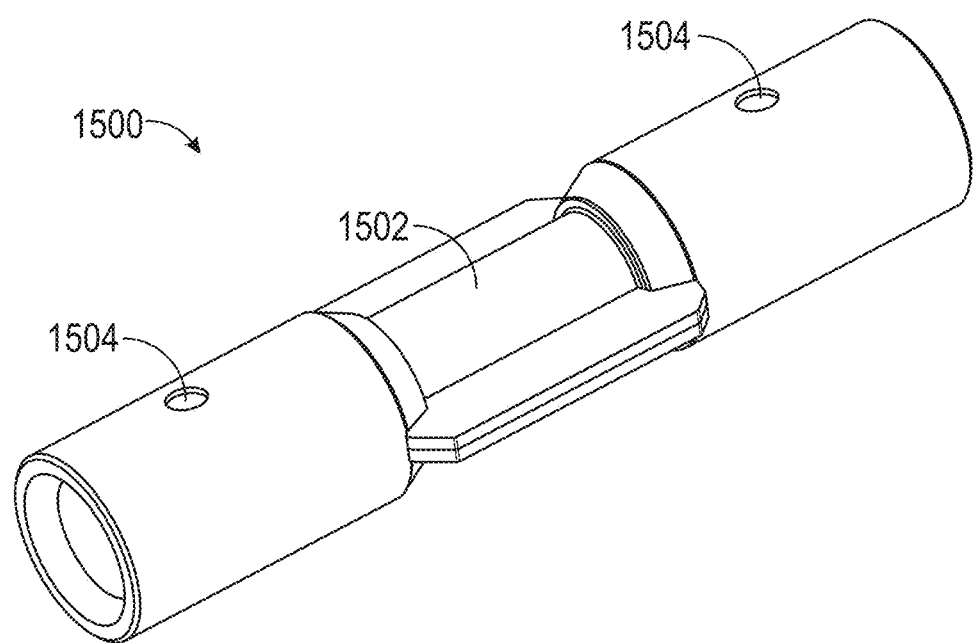
FIG. 15 shows a perspective view of an example of a cuvette.

FIG. 15 shows a schematic diagram of an example of a cuvette. The blood filtration system 100 may include the cuvette 1500. In an example, the cuvette 1500 may be in communication with the blood circuit 120 (shown in FIG. 1). For example, the cuvette 1500 may be in communication with one or more of the withdrawal line 104 or the infusion line 106 (shown in FIG. 1). In another example, fluid (e.g., blood including one or more plasma constituents, or the like) may be withdrawn from vasculature of a patient and flow through the withdrawal line 104, for instance through a withdrawal lumen of the withdrawal line 104. The cuvette 1500 may be in communication with the withdrawal line 104, and fluid flowing through the withdrawal line 104 may flow through the cuvette 1500.

The cuvette 1500 may include an optical window 1502. The optical window 1502 may facilitates measurement of optical characteristics of the fluid in the cuvette 1500. In an example, optical characteristics of the blood include one or more of a wavelength, bandwidth, intensity, frequency, duration, or the like of light transmitted through the fluid and received by an optical sensor. Optical characteristics of the fluid may vary in correspondence with concentrations of substances within the blood, for instance a concentration of red blood cells or a concentration of an imaging substance (e.g., indocyanine green, or the like). In an example, optical characteristics of fluid may vary in correspondence with a hematocrit value of the blood of the patient.

Figure 16:
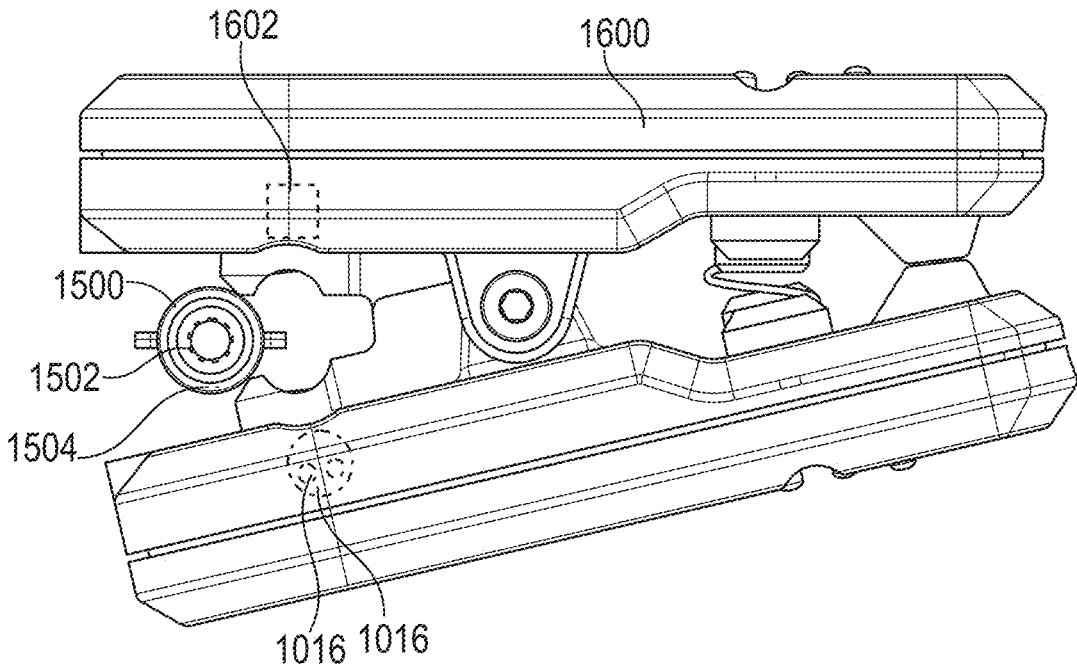
FIG. 16 shows a side view of an example of a blood circuit characteristic sensor and the cuvette of FIG. 15.

FIG. 16 shows a side view of an example of a blood circuit characteristic sensor 1600 and the cuvette 1500. For instance, the blood circuit characteristic sensor 1600 may include an optical sensor 1602. The optical sensor 1602 may measure optical characteristics of fluid in the blood circuit 120 (e.g., fluid in the cuvette 1500, or the like). The optical sensor 1602 may couple with the blood circuit 120, for instance coupling with cuvette 1500. The optical sensor 1602 may transmit light through the cuvette 1500 to measure the optical characteristics of fluid received in the cuvette 1500. For instance, the optical sensor 1602 may transmit light through the optical window 1502 (shown in FIG. 15) of the cuvette 1500.

In an example, the system 100 may use the optical sensor 1602 to determine a hematocrit value of the patient. For instance, system 100 may determine a hematocrit value (e.g., level, or the like) of the patient based on changes in one or more optical characteristics of blood in the cuvette 1500.

Referring to FIGS. 15 and 16, the cuvette 1500 may include one or more acoustic windows 1504. The cuvette 1500 may include the optical window 1502, for instance to facilitate transmission of light through the cuvette 1500 with the optical sensor 1602. The acoustic windows 1504 may have properties to maximize the power transfer of an ultrasonic signal from an applied ultrasonic transducer (e.g., the ultrasonic transducer 1016 (shown in FIG. 10 and FIG. 16) to the blood.

The acoustic windows 1504 may facilitate impedance matching between the cuvette 1500 and the blood circuit characteristic sensor 1600. For instance, the blood circuit characteristic sensor 1600 may include the ultrasonic transducer 1016. The ultrasonic transducer 1016 (e.g., the transmitter 1202, or the like) may generate an ultrasonic signal. The ultrasonic signal may have a specified impedance. The acoustic windows 1504 may have the specified impedance of the ultrasonic signal. In another example, an impedance of the acoustic windows is approximately equal to the specified impedance of the ultrasonic signal. In yet another example, the impedance of the acoustic windows 1504 may correspond with the specified impedance of the ultrasonic signal. Accordingly, coupling the ultrasonic transducer 1016 with the acoustic windows 1504 may reduce attenuation of the ultrasonic signal. Thus, performance of the blood filtration system 100 may be enhanced, for instance because the acoustic windows 1504 have a similar impedance to the ultrasonic signal generated by the ultrasonic transducer 1016. In another example, the acoustic windows 1504 may be aligned with one or more of the transmitter 1202 or the receiver 1204. The alignment between the acoustic windows 1504 and the ultrasonic transducer 1016 may minimize attenuation of an ultrasonic signal transmitted through the cuvette 1500, for instance by minimizing impedance mismatch between ultrasonic signal and the cuvette 1500.

Various Notes & Aspects

Example 1 is a catheter configured for insertion into vasculature of a patient, the catheter comprising: a proximal portion including a hub; a withdrawal lumen wall extending around a withdrawal lumen, wherein: the withdrawal lumen wall extends between the proximal portion and a withdrawal lumen tip, the withdrawal lumen tip configured for reception of blood into the withdrawal lumen from the vasculature; and the withdrawal lumen has a withdrawal lumen profile; an infusion lumen wall coupled with the withdrawal lumen wall, the infusion lumen wall extending around an infusion lumen, wherein: the infusion lumen wall extends between the proximal portion and an infusion lumen tip, the infusion lumen tip configured for discharge of blood into the vasculature from the infusion lumen; the infusion lumen has an infusion lumen profile smaller than the withdrawal lumen profile; a flexible septum extending between the withdrawal lumen and the infusion lumen, wherein: the flexible septum is coupled with the withdrawal lumen wall and the infusion lumen wall; and the flexible septum isolates the withdrawal lumen from the infusion lumen.

In Example 2, the subject matter of Example 1 optionally includes wherein: the withdrawal lumen profile has a first cross-sectional area; and the infusion lumen profile has a second cross-sectional area smaller than the first cross-sectional area.

In Example 3, the subject matter of any one or more of Examples 1-2 optionally include wherein the withdrawal lumen is configured to communicate with the infusion lumen through a filter.

In Example 4, the subject matter of any one or more of Examples 1-3 optionally include a transducer configured to measure one or more fluid flow characteristics of fluid flowing in the vasculature of the patient.

In Example 5, the subject matter of Example 4 optionally includes wherein the transducer is configured for insertion into the vasculature of the patient.

In Example 6, the subject matter of any one or more of Examples 4-5 optionally include wherein the transducer is configured to measure fluid flow characteristics between the catheter and a vasculature wall of the patient.

In Example 7, the subject matter of any one or more of Examples 4-6 optionally include wherein the transducer is configured to measure fluid flow characteristics around the catheter.

In Example 8, the subject matter of any one or more of Examples 4-7 optionally include wherein the catheter includes a withdrawal lumen wall extending around a withdrawal lumen, wherein: the withdrawal lumen wall extends to a withdrawal lumen tip, the withdrawal lumen tip configured for reception of blood into the withdrawal lumen from the vasculature.

Example 9 is a blood filtration system, comprising: a blood circuit including a catheter, the catheter configured for insertion into vasculature of a patient, the catheter including a transducer configured to measure one or more fluid flow characteristics of fluid flowing in the vasculature of the patient with the catheter inserted into the vasculature of the patient; and a controller including: a sensor interface module configured to receive the measured one or more fluid flow characteristics; a pump module configured to modulate one or more of a variable-speed blood pump or a variable-speed filtration pump, wherein: the pump module is configured to modulate the variable-speed blood pump to vary a blood flow rate through the blood circuit; and the pump module is configured to modulate the variable-speed filtrate pump to vary an extraction rate of filtrate fluid from a filter of the blood circuit; a therapy guidance module configured to guide one or more of the blood flow rate or the extraction rate, wherein: the therapy guidance module is configured to change the blood flow rate based on the one or more fluid flow characteristics; and the therapy guidance module is configured to change the extraction rate based on the one or more fluid flow characteristics.

In Example 10, the subject matter of Example 9 optionally includes wherein the transducer is configured for insertion into the vasculature of the patient.

In Example 11, the subject matter of Example 10 optionally includes wherein: the catheter includes a withdrawal lumen wall extending around a withdrawal lumen; the withdrawal lumen wall extends to a withdrawal lumen tip, the withdrawal lumen tip configured for reception of blood into the withdrawal lumen from the vasculature; the transducer is located between a hub of the catheter and the withdrawal lumen tip.

In Example 12, the subject matter of any one or more of Examples 10-11 optionally include wherein the transducer is configured to measure the fluid flow characteristics between a portion of the catheter and a vasculature wall of the vasculature of the patient.

In Example 13, the subject matter of any one or more of Examples 10-12 optionally include wherein the transducer is configured to measure fluid flow characteristics around the catheter.

In Example 14, the subject matter of any one or more of Examples 9-13 optionally include wherein the therapy guidance module is configured to determine a venous flow rate for the fluid flowing in the vasculature of the patient.

In Example 15, the subject matter of Example 14 optionally includes wherein the therapy guidance module is configured to guide the blood flow rate between a minimum blood flow rate and a maximum blood flow rate, with a specified blood flow rate located between the minimum blood flow rate and the maximum blood flow rate.

In Example 16, the subject matter of Example 15 optionally includes wherein: the therapy guidance module is configured to limit the blood flow rate to a maximum blood flow rate and the specified blood flow rate is located at or below the maximum blood flow rate; and the therapy guidance module is configured to establish the maximum blood flow rate based on the determined venous flow rate.

In Example 17, the subject matter of any one or more of Examples 14-16 optionally include wherein: the therapy guidance module is configured to limit the extraction rate to a maximum extraction rate and a specified extraction rate is located at or below the maximum extraction rate; and the therapy guidance module is configured to establish the maximum extraction rate based on the determined venous flow rate.

In Example 18, the subject matter of any one or more of Examples 9-17 optionally include wherein the therapy guidance module is configured to repeatedly determine the venous flow rate for the fluid flowing in the vasculature of the patient.

In Example 19, the subject matter of Example 18 optionally includes wherein: the therapy guidance module limits the blood flow rate to a maximum blood flow rate and the specified blood flow rate is located at or below the maximum blood flow rate; and the therapy guidance module is configured to repeatedly establish the maximum blood flow rate based on the repeatedly determined venous flow rate.

In Example 20, the subject matter of Example 19 optionally includes wherein the therapy guidance module is configured to repeatedly establish the maximum blood flow rate in proportion to the repeatedly determined venous flow rate.

In Example 21, the subject matter of any one or more of Examples 19-20 optionally include wherein: the therapy guidance module is configured to limit the extraction rate to a maximum extraction rate and the specified extraction rate is located at or below the maximum extraction rate; and the therapy guidance module is configured to repeatedly establish the maximum extraction rate based on the determined venous flow rate.

In Example 22, the subject matter of any one or more of Examples 18-21 optionally include wherein: the therapy guidance module is configured to guide the blood flow rate within a range of blood flow rates including the specified blood flow rate; the therapy guidance module limits the range of blood flow rates to a maximum blood flow rate and the specified blood flow rate is located at or below the maximum blood flow rate; and the therapy guidance module is configured to repeatedly establish the maximum blood flow rate based on the repeatedly determined venous flow rate.

In Example 23, the subject matter of any one or more of Examples 18-22 optionally include wherein: the therapy guidance module is configured to limit the extraction rate to a maximum extraction rate and the specified extraction rate is located at or below the maximum extraction rate; and the therapy guidance module is configured to repeatedly establish the maximum extraction rate based on the determined venous flow rate.

In Example 24, the subject matter of Example 23 optionally includes wherein the therapy guidance module is configured to repeatedly establish the maximum extraction rate in proportion to the repeatedly determined venous flow rate.

In Example 25, the subject matter of any one or more of Examples 18-24 optionally include wherein: the therapy guidance module is configured to guide the extraction rate within a range of extraction rates including the specified extraction rate; the therapy guidance module limits the range of extraction rates to a maximum extraction rate and the specified extraction rate is located at or below the maximum extraction rate; and the therapy guidance module is configured to repeatedly establish the maximum extraction rate based on the repeatedly determined venous flow rate.

In Example 26, the subject matter of any one or more of Examples 9-25 optionally include wherein the transducer includes one or more sonic emitters and one or more sonic receivers.

In Example 27, the subject matter of any one or more of Examples 9-26 optionally include a withdrawal flow sensor configured to measure flow rate of the fluid in the withdrawal lumen.

Example 28 is a blood filtration system, comprising: a blood circuit including a catheter, the catheter configured for insertion into vasculature of a patient, wherein the catheter includes a withdrawal lumen and an infusion lumen, each of the withdrawal lumen and the infusion lumen configured for transmitting fluid including blood; an extracorporeal flow rate sensor configured to measure flow rate of the fluid in one or more of the withdrawal lumen or the infusion lumen; a controller having processing circuitry, the controller including: a sensor interface module configured to receive the measured flow rate; a pump module configured to modulate a variable-speed pump to vary a flow rate of the fluid through one or more of the withdrawal lumen or the infusion lumen; and a therapy guidance module configured to guide the measured flow rate toward a specified blood circuit flow rate by cooperating with the pump module to modulate the variable-speed pump.

In Example 29, the subject matter of Example 28 optionally includes wherein the extracorporeal flow rate sensor includes: a first sonic emitter configured to transmit a first acoustic signal in a first direction through one or more of the withdrawal lumen or the infusion lumen; a second sonic emitter configured to transmit a second acoustic signal in a second direction through one or more of the withdrawal lumen or the infusion lumen, the second direction offset from the first direction; a first sonic receiver configured to receive at least the first acoustic signal; and a second sonic receiver configured to receive at least the second acoustic signal, wherein the first sonic receiver is spaced apart from the second sonic receiver.

In Example 30, the subject matter of Example 29 optionally includes wherein: the first sonic emitter is configured to transmit the first acoustic signal through the withdrawal lumen; the second sonic emitter is configured to transmit the second acoustic signal through the withdrawal lumen; and the first sonic receiver and the second sonic receiver are spaced apart along the withdrawal lumen.

In Example 31, the subject matter of Example 30 optionally includes wherein the first direction is offset at an angle with respect to the second direction.

In Example 32, the subject matter of Example 31 optionally includes degrees or more with respect to the second direction.

In Example 33, the subject matter of Example 32 optionally includes degrees with respect to the second direction.

Example 34 is a catheter, comprising: an infusion lumen wall extending to an infusion lumen tip, wherein: the infusion lumen wall surrounds an infusion lumen; the infusion lumen is configured for fluidic communication with an infusion line of a blood filtration system; the infusion lumen is configured to discharge fluid at the infusion lumen tip, the fluid supplied by the blood filtration system; a withdrawal lumen wall extending from a proximal section to a withdrawal lumen tip, wherein: the withdrawal lumen tip is included in the distal section of the withdrawal lumen wall; the withdrawal lumen wall surrounds a withdrawal lumen; the withdrawal lumen is configured for fluidic communication with a withdrawal line of the blood filtration system; the infusion lumen is isolated from the withdrawal lumen; the withdrawal lumen is configured to receive fluid from vasculature of a patient at the withdrawal lumen tip; the withdrawal lumen wall extends beyond the infusion lumen tip to longitudinally offset the withdrawal lumen tip from the infusion lumen tip; the withdrawal lumen wall includes a transition section extending between the proximal section and the distal section; and the catheter includes a central axis, and the transition section extends across the central axis of the catheter.

In Example 35, the subject matter of Example 34 optionally includes wherein the withdrawal lumen wall includes: a polymeric material; a first structural support section including one or more structural supports embedded in the polymeric material; and a second structural support section including the one or more structural supports, wherein the second structural support section is separated from the first structural support section by a first trimming section of the polymeric material located between the first structural support section and the second structural support section.

In Example 36, the subject matter of Example 35 optionally includes wherein the first structural support, the second structural support and the first trimming section are located in the proximal section of the withdrawal lumen wall.

In Example 37, the subject matter of Example 36 optionally includes wherein a distal section of withdrawal lumen wall includes: a third structural support section including the one or more structural supports embedded in the polymeric material; and a fourth structural support section including the one or more structural supports, wherein the fourth structural support section is separated from the third structural support section by a second trimming section of the polymeric material located between the third structural support section and the fourth structural support section.

In Example 38, the subject matter of Example 37 optionally includes wherein the second trimming section is included in a plurality of trimming sections, and the plurality of trimming sections are included in the distal section of the withdrawal lumen wall.

In Example 39, the subject matter of Example 38 optionally includes wherein the plurality of trimming sections facilitate user-customization of a length of the withdrawal lumen wall between a hub of the catheter and the withdrawal lumen tip.

In Example 40, the subject matter of any one or more of Examples 35-39 optionally include wherein the withdrawal lumen wall includes: a third structural support section including the one or more structural supports embedded in the polymeric material; and a fourth structural support section including the one or more structural supports, wherein the fourth structural support section is separated from the third structural support section by a second trimming section of the polymeric material located between the third structural support section and the fourth structural support section.

In Example 41, the subject matter of any one or more of Examples 34-40 optionally include a transducer configured to measure one or more fluid flow characteristics of fluid flowing in the vasculature of the patient.

In Example 42, the subject matter of Example 41 optionally includes wherein the transducer is configured to measure fluid flow characteristics between the catheter and a vasculature wall of the patient.

In Example 43, the subject matter of any one or more of Examples 41-42 optionally include wherein the transducer is configured to measure fluid flow characteristics around the catheter.

In Example 44, the subject matter of any one or more of Examples 34-43 optionally include a ferromagnetic member included in the withdrawal lumen wall, wherein: the ferromagnetic member is located proximate the withdrawal lumen tip; and the ferromagnetic member is configured for detection by a sensor ex vivo to vasculature of the patient.

In Example 45, the subject matter of any one or more of Examples 34-44 optionally include wherein the infusion lumen wall and the withdrawal lumen wall cooperate to isolate the infusion lumen from the withdrawal lumen.

Each of these non-limiting examples can stand on its own, or can be combined in various permutations or combinations with one or more of the other examples.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A catheter, comprising:
an infusion lumen wall extending to an infusion lumen tip, wherein:
the infusion lumen wall surrounds an infusion lumen;
the infusion lumen is in fluidic communication with an infusion line of a blood filtration system; and
the infusion lumen discharges fluid at the infusion lumen tip, the fluid supplied by the blood filtration system;
a withdrawal lumen wall extending from a proximal section to a withdrawal lumen tip, wherein:
the withdrawal lumen tip is included in a distal section of the withdrawal lumen wall;
the withdrawal lumen wall surrounds a withdrawal lumen;
the withdrawal lumen is in fluidic communication with a withdrawal line of the blood filtration system;
the infusion lumen is isolated from the withdrawal lumen;
the withdrawal lumen is located and arranged to receive fluid from vasculature of a patient at the withdrawal lumen tip;
the withdrawal lumen wall includes a polymeric material;

the withdrawal lumen wall has a first structural support section including one or more structural supports embedded in the polymeric material;

the withdrawal lumen wall has a second structural support section including the one or more structural supports, wherein the second structural support section is separated from the first structural support section by a first trimming section of the polymeric material located between the first structural support section and the second structural support section, wherein the first trimming section includes a continuous fluid-impervious outer wall section and does not include the one or more structural supports, and wherein the first trimming section is included in a plurality of trimming sections, which include a continuous fluid-impervious outer wall section and which do not include the one or more structure supports, that are included in the distal section of the withdrawal lumen wall and are individually arranged and spaced apart from each other to ease cutting during user-customization of a length of the withdrawal lumen wall between a hub of the catheter and the withdrawal lumen tip;

the withdrawal lumen wall extends beyond the infusion lumen tip to longitudinally offset the withdrawal lumen tip from the infusion lumen tip;

the withdrawal lumen wall includes a transition section extending between the proximal section and the distal section; and the catheter includes a central axis, and the transition section extends across the central axis of the catheter.

2. The catheter of claim 1, the catheter comprising:

a proximal portion including the hub;

wherein the withdrawal line is a negative pressure withdrawal line that is connected to a negative pressure source of the blood filtration system providing a negative pressure in the withdrawal lumen;

the infusion lumen is in fluidic communication with a positive pressure infusion line that is connected to a positive pressure source providing a positive pressure in the infusion lumen;

a flexible septum extending between the withdrawal lumen and the infusion lumen, wherein:

the flexible septum is coupled with the withdrawal lumen wall and the infusion lumen wall; and the flexible septum isolates the withdrawal lumen from the infusion lumen; and wherein, in use, the flexible septum deflects toward the infusion lumen to offset a difference in fluid flow between the infusion lumen and the withdrawal lumen to equalize a pressure differential between the positive pressure in the infusion lumen and the negative pressure in the withdrawal lumen to compensate for fluid removal by the blood filtration system attached to the withdrawal lumen such that less fluid is returned to the infusion lumen than withdrawn by the withdrawal lumen.

3. The catheter of claim 2, further comprising a transducer capable of measuring one or more fluid flow characteristics of fluid flowing in the vasculature of the patient.

4. The catheter of claim 3, wherein the transducer is sized and shaped for insertion into the vasculature of the patient.

5. The catheter of claim 3, wherein the transducer is capable of measuring one or more fluid flow characteristics between the catheter and a vasculature wall of the patient.

6. The catheter of claim 3, wherein the transducer is capable of measuring one or more fluid flow characteristics around the catheter.

7. The catheter of claim 2, wherein the withdrawal lumen tip is located more distally than an infusion lumen tip to inhibit recapture of non-circulated fluid dispensed via the infusion lumen tip.

8. The catheter of claim 1, wherein the first structural support, the second structural support and the first trimming section are located in the proximal section of the withdrawal lumen wall.

9. The catheter of claim 8, wherein a distal section of withdrawal lumen wall includes:

a third structural support section including the one or more structural supports embedded in the polymeric material; and a fourth structural support section including the one or more structural supports, wherein the fourth structural support section is separated from the third structural support section by a second trimming section of the polymeric material located between the third structural support section and the fourth structural support section.

10. The catheter of claim 9, wherein the second trimming section is included in the plurality of trimming sections, and the plurality of trimming sections are included in the distal section of the withdrawal lumen wall.

11. The catheter of claim 1, wherein the withdrawal lumen wall includes:

a third structural support section including the one or more structural supports embedded in the polymeric material; and a fourth structural support section including the one or more structural supports, wherein the fourth structural support section is separated from the third structural support section by a second trimming section of the polymeric material located between the third structural support section and the fourth structural support section.

* * * * *